United States Patent
Dinsmoor et al.

(10) Patent No.: US 12,023,501 B2
(45) Date of Patent: *Jul. 2, 2024

(54) ECAP BASED CONTROL OF ELECTRICAL STIMULATION THERAPY

(71) Applicant: Medtronic, Inc., Minneapolis, MN (US)

(72) Inventors: David A. Dinsmoor, North Oaks, MN (US); Kristin N. Hageman, Dayton, MN (US); Hank Bink, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 202 days.

This patent is subject to a terminal disclaimer.

(21) Appl. No.: 17/484,912

(22) Filed: Sep. 24, 2021

(65) Prior Publication Data

US 2022/0008731 A1    Jan. 13, 2022

Related U.S. Application Data

(63) Continuation of application No. 16/449,168, filed on Jun. 21, 2019, now Pat. No. 11,129,991.

(Continued)

(51) Int. Cl.
*A61N 1/36* (2006.01)

(52) U.S. Cl.
CPC ..... *A61N 1/36178* (2013.01); *A61N 1/36153* (2013.01); *A61N 1/36175* (2013.01)

(58) Field of Classification Search
None
See application file for complete search history.

(56) References Cited

U.S. PATENT DOCUMENTS

| 5,603,726 A | 2/1997 | Schulman et al. |
| 5,800,465 A | 9/1998 | Thompson et al. |

(Continued)

FOREIGN PATENT DOCUMENTS

| CN | 105031812 A | 11/2015 |
| CN | 105407964 A | 3/2016 |

(Continued)

OTHER PUBLICATIONS

Youn et al., The Effect of High-Frequency Stimulation on Sensory Thresholds in Chronic Pain Patients, Stereotact Funct Neurosurg 2015; 93:355-359 (Year: 2015).*

(Continued)

*Primary Examiner* — Carl H Layno
*Assistant Examiner* — Manolis Pahakis
(74) *Attorney, Agent, or Firm* — Shumaker & Sieffert, P.A.

(57) ABSTRACT

Devices, systems, and techniques for controlling electrical stimulation therapy are described. In one example, a system may be configured to deliver electrical stimulation therapy to a patient, the electrical stimulation therapy comprising a plurality of therapy pulses at a predetermined pulse frequency over a period of tune and deliver, over the period of time, a plurality of control pulses interleaved with at least some therapy pulses of the plurality of therapy pulses. The system may also be configured to sense, after one or more control pulses and prior to an immediately subsequent therapy pulse of the plurality of therapy pulses, a respective evoked compound action potential (ECAP), adjust, based on at least one respective ECAP, one or more parameter values that at least partially defines the plurality of therapy pulses, and deliver the electrical stimulation therapy to the patient according to the adjusted one or more parameter values.

19 Claims, 15 Drawing Sheets

Related U.S. Application Data

(60) Provisional application No. 62/688,223, filed on Jun. 21, 2018.

(56) References Cited

U.S. PATENT DOCUMENTS

| | | | |
|---|---|---|---|
| 6,157,861 A | 12/2000 | Faltys et al. | |
| 6,205,360 B1 | 3/2001 | Carter | |
| 6,289,247 B1 | 9/2001 | Faltys et al. | |
| 6,314,325 B1 | 11/2001 | Fitz | |
| 6,421,566 B1 | 7/2002 | Holsheimer | |
| 6,505,078 B1 | 1/2003 | King et al. | |
| 6,675,046 B2 | 1/2004 | Holsheimer | |
| 6,850,802 B2 | 2/2005 | Holsheimer | |
| 6,988,006 B2 | 1/2006 | King et al. | |
| 7,076,292 B2 | 7/2006 | Forsberg | |
| 7,206,640 B1 | 4/2007 | Overstreet | |
| 7,333,858 B2 | 2/2008 | Killian et al. | |
| 7,450,992 B1 | 11/2008 | Cameron | |
| 7,577,480 B2 | 8/2009 | Zeijlemaker | |
| 7,616,999 B2 | 11/2009 | Overstreet et al. | |
| 7,657,318 B2 | 2/2010 | King et al. | |
| 7,689,289 B2 | 3/2010 | King | |
| 7,742,810 B2 | 6/2010 | Moffitt et al. | |
| 7,792,583 B2 | 9/2010 | Miesel et al. | |
| 8,036,747 B2 | 10/2011 | Thacker et al. | |
| 8,090,446 B2 * | 1/2012 | Fowler | A61N 1/36025 607/45 |
| 8,504,150 B2 * | 8/2013 | Skelton | A61N 1/37264 607/30 |
| 8,620,441 B2 | 12/2013 | Greenberg et al. | |
| 8,676,329 B2 * | 3/2014 | Wacnik | A61N 1/36071 607/46 |
| 8,694,108 B2 | 4/2014 | Alataris et al. | |
| 8,708,934 B2 | 4/2014 | Skelton et al. | |
| 8,712,533 B2 | 4/2014 | Alataris et al. | |
| 8,712,534 B2 | 4/2014 | Wei | |
| 8,751,009 B2 | 6/2014 | Wacnik | |
| 8,897,888 B2 | 11/2014 | Parker et al. | |
| 8,923,984 B2 | 12/2014 | Parker et al. | |
| 9,002,460 B2 | 4/2015 | Parker | |
| 9,072,910 B2 | 7/2015 | Parker et al. | |
| 9,089,714 B2 | 7/2015 | Robinson | |
| 9,089,715 B2 | 7/2015 | Parker et al. | |
| 9,138,582 B2 | 9/2015 | Doan et al. | |
| 9,155,892 B2 | 10/2015 | Parker et al. | |
| 9,283,373 B2 | 3/2016 | Parker et al. | |
| 9,302,112 B2 | 4/2016 | Bornzin et al. | |
| 9,339,655 B2 | 5/2016 | Carbunaru | |
| 9,364,667 B1 | 6/2016 | Dinsmoor et al. | |
| 9,381,356 B2 | 7/2016 | Parker et al. | |
| 9,386,934 B2 | 7/2016 | Parker et al. | |
| 9,387,325 B1 | 7/2016 | Min et al. | |
| 9,566,439 B2 | 2/2017 | Single et al. | |
| 9,597,507 B2 | 3/2017 | Johanek et al. | |
| 9,700,713 B2 | 7/2017 | Robinson et al. | |
| 9,872,990 B2 | 1/2018 | Parker et al. | |
| 9,993,646 B2 * | 6/2018 | Parramon | A61N 1/36132 |
| 10,183,168 B2 | 1/2019 | Baru et al. | |
| 10,569,088 B2 | 2/2020 | Dinsmoor et al. | |
| 10,588,524 B2 * | 3/2020 | Single | A61B 5/4041 |
| 10,933,242 B2 | 3/2021 | Torgerson | |
| 11,524,163 B2 | 12/2022 | Baynham et al. | |
| 2004/0267333 A1 | 12/2004 | Kronberg | |
| 2008/0221640 A1 | 9/2008 | Overstreet et al. | |
| 2008/0300655 A1 | 12/2008 | Cholette | |
| 2011/0046432 A1 | 2/2011 | Simon et al. | |
| 2011/0054570 A1 | 3/2011 | Lane | |
| 2011/0071589 A1 | 3/2011 | Starkebaum et al. | |
| 2011/0077712 A1 * | 3/2011 | Killian | A61B 5/12 607/57 |
| 2011/0125223 A1 | 5/2011 | Carbunaru et al. | |
| 2012/0155188 A1 | 6/2012 | Buettner et al. | |
| 2012/0226332 A1 | 9/2012 | Chambers | |
| 2013/0208390 A1 | 8/2013 | Singh et al. | |
| 2013/0268021 A1 | 10/2013 | Moffitt | |
| 2013/0289664 A1 | 10/2013 | Johanek | |
| 2013/0289683 A1 | 10/2013 | Parker et al. | |
| 2014/0005753 A1 * | 1/2014 | Carbunaru | A61N 1/0551 607/72 |
| 2014/0025146 A1 | 1/2014 | Alataris et al. | |
| 2014/0031896 A1 | 1/2014 | Alataris et al. | |
| 2014/0031905 A1 | 1/2014 | Irazoqui et al. | |
| 2014/0074189 A1 | 3/2014 | Moffitt | |
| 2014/0142656 A1 | 5/2014 | Alataris et al. | |
| 2014/0142673 A1 | 5/2014 | Alataris et al. | |
| 2014/0194772 A1 | 7/2014 | Single et al. | |
| 2014/0236042 A1 | 8/2014 | Parker et al. | |
| 2014/0236257 A1 * | 8/2014 | Parker | A61B 5/4041 607/46 |
| 2014/0243924 A1 * | 8/2014 | Zhu | A61N 1/36146 607/46 |
| 2014/0243926 A1 | 8/2014 | Carcieri et al. | |
| 2014/0243931 A1 | 8/2014 | Parker et al. | |
| 2014/0277267 A1 | 9/2014 | Vansickle | |
| 2014/0277282 A1 | 9/2014 | Jaax | |
| 2014/0288577 A1 | 9/2014 | Robinson et al. | |
| 2014/0293737 A1 | 10/2014 | Parker et al. | |
| 2014/0296936 A1 | 10/2014 | Alataris et al. | |
| 2014/0324143 A1 | 10/2014 | Robinson et al. | |
| 2014/0371813 A1 | 12/2014 | King et al. | |
| 2014/0378941 A1 | 12/2014 | Su et al. | |
| 2014/0379043 A1 | 12/2014 | Howard | |
| 2015/0005842 A1 | 1/2015 | Lee et al. | |
| 2015/0012068 A1 | 1/2015 | Bradley et al. | |
| 2015/0032181 A1 | 1/2015 | Baynham et al. | |
| 2015/0039057 A1 * | 2/2015 | Della Santina | A61N 1/36103 607/116 |
| 2015/0057729 A1 | 2/2015 | Parker et al. | |
| 2015/0127062 A1 | 5/2015 | Holley et al. | |
| 2015/0179177 A1 | 6/2015 | Nagao | |
| 2015/0282725 A1 | 10/2015 | Single | |
| 2015/0313487 A1 | 11/2015 | Single et al. | |
| 2015/0360031 A1 | 12/2015 | Bornzin et al. | |
| 2015/0374999 A1 | 12/2015 | Parker et al. | |
| 2016/0082252 A1 * | 3/2016 | Hershey | A61N 1/36071 607/46 |
| 2016/0121124 A1 | 5/2016 | Johanek et al. | |
| 2016/0129272 A1 | 5/2016 | Hou et al. | |
| 2016/0136420 A1 * | 5/2016 | Brink | A61N 1/36007 607/41 |
| 2016/0157769 A1 | 6/2016 | Min et al. | |
| 2016/0158550 A1 | 6/2016 | Hou et al. | |
| 2016/0158551 A1 * | 6/2016 | Kent | A61N 1/36167 607/46 |
| 2016/0166164 A1 | 6/2016 | Obradovic et al. | |
| 2016/0175594 A1 | 6/2016 | Min et al. | |
| 2016/0206883 A1 * | 7/2016 | Bornzin | A61N 1/36182 |
| 2016/0287126 A1 | 10/2016 | Parker et al. | |
| 2016/0287182 A1 * | 10/2016 | Single | A61B 5/24 |
| 2016/0303368 A1 | 10/2016 | Parramon et al. | |
| 2016/0346534 A1 | 12/2016 | Isaacson et al. | |
| 2016/0361542 A1 | 12/2016 | Kaula et al. | |
| 2017/0001017 A9 | 1/2017 | Parker et al. | |
| 2017/0049345 A1 | 2/2017 | Single | |
| 2017/0071490 A1 | 3/2017 | Parker et al. | |
| 2017/0135624 A1 | 5/2017 | Parker | |
| 2017/0173332 A1 * | 6/2017 | Overstreet | A61N 1/36039 |
| 2017/0209695 A1 | 7/2017 | Solomon | |
| 2017/0216587 A1 | 8/2017 | Parker | |
| 2017/0216602 A1 | 8/2017 | Waataja et al. | |
| 2017/0296823 A1 | 10/2017 | Hershey et al. | |
| 2017/0361101 A1 * | 12/2017 | Single | A61N 1/0551 |
| 2017/0361103 A1 * | 12/2017 | Hadjiyski | A61N 1/0551 |
| 2018/0056073 A1 | 3/2018 | Torgerson | |
| 2018/0078769 A1 * | 3/2018 | Dinsmoor | A61N 1/36007 |
| 2018/0110987 A1 | 4/2018 | Parker | |
| 2018/0117332 A1 | 5/2018 | Robinson et al. | |
| 2018/0117335 A1 | 5/2018 | Parker et al. | |
| 2018/0126169 A1 | 5/2018 | Hou et al. | |
| 2018/0132760 A1 | 5/2018 | Parker | |
| 2018/0140830 A1 | 5/2018 | Marnfeldt et al. | |
| 2018/0154144 A1 * | 6/2018 | Brink | A61N 1/36171 |
| 2018/0200520 A1 * | 7/2018 | Tranchina | A61N 1/36139 |

(56) References Cited

U.S. PATENT DOCUMENTS

| | | | |
|---|---|---|---|
| 2018/0214701 A1 | 8/2018 | Zhang et al. | |
| 2018/0256897 A1 | 9/2018 | Parramon | |
| 2019/0099601 A1* | 4/2019 | Torgerson | A61B 5/4848 |
| 2019/0105496 A1 | 4/2019 | Min et al. | |
| 2019/0209844 A1 | 7/2019 | Esteller et al. | |
| 2019/0247657 A1 | 8/2019 | Brill et al. | |
| 2019/0388692 A1* | 12/2019 | Dinsmoor | A61N 1/36071 |
| 2019/0388695 A1* | 12/2019 | Dinsmoor | G16H 20/30 |
| 2020/0038660 A1* | 2/2020 | Torgerson | A61N 1/36135 |
| 2020/0101294 A1 | 4/2020 | Torgerson | |
| 2020/0171312 A1 | 6/2020 | Dinsmoor et al. | |
| 2020/0171313 A1 | 6/2020 | Dinsmoor et al. | |
| 2021/0101007 A1 | 4/2021 | Hamner et al. | |
| 2021/0121698 A1* | 4/2021 | Dinsmoor | A61N 1/36153 |
| 2021/0121699 A1* | 4/2021 | Dinsmoor | A61N 1/36192 |
| 2021/0121700 A1 | 4/2021 | Dinsmoor et al. | |
| 2021/0187299 A1* | 6/2021 | Dinsmoor | A61N 1/36135 |
| 2021/0236821 A1 | 8/2021 | Sinclair et al. | |
| 2022/0008730 A1 | 1/2022 | Dinsmoor et al. | |

FOREIGN PATENT DOCUMENTS

| | | |
|---|---|---|
| EP | 2396072 B1 | 3/2013 |
| EP | 3013413 A1 | 5/2016 |
| EP | 3024540 B1 | 10/2018 |
| WO | 2002009808 A1 | 2/2002 |
| WO | 2007117232 A1 | 10/2007 |
| WO | 2010058178 A1 | 5/2010 |
| WO | 2012155188 A1 | 11/2012 |
| WO | 2014138990 A1 | 9/2014 |
| WO | 2014210373 A1 | 12/2014 |
| WO | 2015143509 A1 | 10/2015 |
| WO | 2015179177 A1 | 11/2015 |
| WO | 2015179281 A2 | 11/2015 |
| WO | 2016090420 A1 | 6/2016 |
| WO | 2016090436 A1 | 6/2016 |
| WO | 2016191808 A1 | 12/2016 |
| WO | 2017100866 A1 | 6/2017 |
| WO | 2017106503 A1 | 6/2017 |
| WO | 2017173493 A1 | 10/2017 |
| WO | 2017184238 A1 | 10/2017 |
| WO | 2017219096 A1 | 12/2017 |
| WO | 2018080753 A1 | 5/2018 |
| WO | 2018080754 A1 | 5/2018 |
| WO | 2018106813 A1 | 6/2018 |
| WO | 2019231794 A1 | 12/2019 |

OTHER PUBLICATIONS

U.S. Appl. No. 17/484,848, filed Sep. 24, 2021, naming inventors Dinsmoor et al.
"St. Jude's Prodigy Neurostimulator with Burst Technology," Medgadget, Mar. 20, 2014, 4 pp.
Abejon MD "Back pain coverage with spinal cord stimulation: A different treatment for each patient," International Neuromodulation Society. Jun. 10, 2015; 567, Abstract Only, 1 pp.
Abeloos MD "High density stimulation as an alternative to uncomfortable cervical tonic spinal cord stimulation: case report," International Neuromodulation Society 12th World Congress, Jun. 11-15, 2015, Abstract Only, 1 pp.
Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.
Breel et al., "High Density Stimulation: A novel programming paradigm for the treatment of chronic pain," International Neuromodulation Society (INS) 12th World Congress; Jun. 9, 2015, Abstract Only, 1 pp.
Crosby et al., "Modulation of activity and conduction in single dorsal column axons by kilohertz-frequency spinal cord stimulation," American Physiological Society, published online Oct. 19, 2016, 27 pp.

Cuellar MD PhD, et al., "Effect of high-frequency alternating current on spinal afferent nociceptive transmission," Neuromodulation: Technology at the Neural Interface; Jul.-Aug. 2013;16(4): pp. 318-327.
Cui et al., "Effect of spinal cord stimulation on tactile hypersensitivity in mononeuropathic rats is potentiated by simultaneous GABA. sub B. and adenosine receptor activation," Neuroscience Letters 247: Apr. 1998; pp. 183-186.
Cui et al., "Spinal cord stimulation attenuates augmented dorsal horn release of excitatory amino acids in mononeuropathy via a GABAergic mechanism," Pain 73, Oct. 1997, pp. 87-95.
De Ridder et al., "Burst spinal cord stimulation for limb and back pain," World neurosurgery, Nov. 2013; 80(5):642-649, e641.
De Ridder MD PhD et al., "Burst spinal cord stimulation: toward paresthesia-free pain suppression," Neurosurgery. May 2010; 66(5): 986-990.
Downey, "Asynchronous Neuromuscular Electrical Stimulation," University of Florida, 2015, accessed on Jul. 18, 2016, 107 pp.
Duyvendak MD et al., "High density stimulation: a novel programming paradigm for the treatment of chronic back and leg pain," Abstracts, International Neuromodulation Society 12th World Congress: Jun. 11-15, 2015, 1 pp.
Gao et al., "Effects of spinal cord stimulation with "standard clinical" and higher frequencies on peripheral blood flow in rats," Brain Res., 1313: (2010) available online Dec. 3, 2009 pp. 53-61.
Grider DO/PhD et al., "High Frequency (1000 Hz) Stimulation Using Commercially Available Implantable Pulse Generator," North American Neuromodulation Society. Dec. 2013, Abstract Only, 2 pp.
Guan MD PhD et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.
Guan, "Spinal Cord Stimulation: Neurophysiological and Neurochemical Mechanisms of Action" Curr Pain Headache Rep DOI 10.1007s11916-014-0260-4, Mar. 8, 2012, pp. 217-225.
Holsheimer, "Computer modelling of spinal cord stimulation and its contribution to therapeutic efficacy," Spinal Cord Aug. 1998, 36: pp. 531-540.
Hubscher et al., "Convergence and cross talk in urogenital neural circuitries," J. Neurophysiol 110: 1997-2005, first published Aug. 7, 2013, 9 pp.
Hunt et al. The molecular dynamics of pain control. Nat Rev Neurosci. Feb. 2001;2(2):83-91.
International Preliminary Report on Patentability from International Application No. PCT/US2019/038579, dated Dec. 30, 2020, 8 pp.
International Search Report and Written Opinion of International Application No. PCT/US2019/038579, dated Sep. 12, 2019, 14 pp.
Kemler MD et al., "Spinal cord stimulation in patients with chronic reflex sympathetic dystrophy," N Engl J Med, Aug. 31, 2000; 343(9):pp. 618-624.
Kilgore PhD et al., "Reversible Nerve Conduction Block Using Kilohertz Frequency Alternating Current," Neuromodulation. Aug. 2013, pp. 242-255.
Kumar et al., "Spinal cord stimulation versus conventional medical management for neuropathic pain: a multicentre randomised controlled trial in patients with failed back surgery syndrome," Pain Jul. 2007; 132(1-2): 179-188.
Likar et al., "High density spinal cord stimulation: a multi-center experience," Abstracts, International Neuromodulation Society 12th World Congress; Jun. 11-15, 2015, 1 pp.
Maeda et al., "Increased c-fos immunoreactivity in the spinal cord and brain following spinal cord stimulation is frequency-dependent," Brain Res. Mar. 9, 2009;1259: pp. 40-50, available online Jan. 6, 2009.
Maeda et al., "Low frequencies, but not high frequencies of bi-polar spinal cord stimulation reduce cutaneous and muscle hyperalgesia induced by nerve injury," Pain; Feb. 2008; 138(1): pp. 143-152.
Maggi et al., "Effect of urethane anesthesia on the micturition reflex in capsaicin-treated rats." Journal of the Autonomic Nervous System, Jan. 1990, 30(3): 247-251.

(56) References Cited

OTHER PUBLICATIONS

North MD et al., "Clinical outcomes of 1 kHz subperception spinal cord stimulation (SCS): Results of a prospective randomized controlled crossover trial," Abstracts, International Neuromodulation Society, Jun. 2015, 1 pp.
North MD et al., "Spinal cord stimulation versus repeated lumbosacral spine surgery for chronic pain: a randomized, controlled trial," Neurosurgery, Jan. 2005; 56(1): 98-106; discussion 106-107.
Ranck JR. et al., "Which elements are excited in electrical stimulation of mammalian central nervous system: a review," Brain Research, Nov. 21, 1975; 98(3): pp. 417-440.
Replogle MD. et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato et al., "Spinal cord stimulation reduces hypersensitivity through activation of opioid receptors in a frequency-dependent manner," Eur J Pain. Apr. 2013 (4): pp. 551-561, first published Oct. 5, 2012.
Schu MD, PhD. et al., "A prospective, randomised, double-blind, placebo-controlled study to examine the effectiveness of burst spinal cord stimulation patterns for the treatment of failed back surgery syndrome," Neuromodulation. Apr. 2014; 17(5): pp. 443-450.
Shechter MD et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith et al., "Successful use of high-frequency spinal cord stimulation following traditional treatment failure," Stereotact Funct Neurosurg. Apr. 1, 2015; 93(3): pp. 190-193.
Snellings et al., "Effects of stimulation site and stimulation parameters on bladder inhibition by electrical nerve stimulation," BJU International, Jul. 2012, pp. 136-143, first published Jan. 19, 2012.
Song MD Phd. et al., "Efficacy of kilohertz-frequency and conventional spinal cord stimulation in rat models of different pain conditions," Neuromodulation Jan. 2014; 17(3): pp. 226-234.
Sweet MD et al., "High Frequency vs. Burst Stimulation Patterns for Dorsal column Stimulation: The Importance of Charge," American Association of Neurological Surgeons, Abstract, Apr. 4, 2014, 2 pp.
Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.
Walter et al., "Inhibiting the hyperreflexic bladder with electrical stimulation in a spinal animal model." Neurourology and Urodynamics, 1993, 12:241-253. doi: 10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.
Wille MD et al., "Altering Conventional to High Density Spinal Cord Stimulation: An Energy Dose-Response Relationship in Neuropathic Pain Therapy," Neuromodulation 2016, Aug. 2016, 9 pp.
Woock et al., "Activation and inhibition of the micturition reflex by penile afferents in the cat," Am J. Physiol Regul Intergre Comp Physiol, published Apr. 23, 2008, pp. R1880-R1889.
Youn et al., The Effect of High-Frequency Stimulation on Sensory Thresholds in Chronic Pain Patients, Stereotact Funct Neurosurg, Oct. 8, 2015, pp. 355-359.
Prosecution History from U.S. Appl. No. 16/449,152, dated Jan. 6, 2021 through Jul. 14, 2021, 79 pp.
Prosecution History from U.S. Appl. No. 16/449,168, dated Jan. 8, 2021 through Jul. 14, 2021, 58 pp.
Decision of Rejection, and translation thereof, from counterpart Japanese Application No. 2020569752 dated May 29, 2023, 12 pp.
U.S. Appl. No. 18/038,434, filed Dec. 22, 2021, naming inventors Dinsmoor et al.
Office Action from U.S. Appl. No. 17/484,848 dated Aug. 9, 2023, 18 pp.
Response to Office Action dated Aug. 9, 2023 from U.S. Appl. No. 17/484,848, filed Nov. 9, 2023, 13 pp.
Communication pursuant to Article 94(3) EPC from counterpart European Application No. 19744916.8 dated Nov. 10, 2023, 4 pp.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
First Examination Report from counterpart Australian Application No. 2019288752 dated Mar. 5, 2024, 3 pp.
First Office Action and Search Report, and translation thereof, from counterpart Chinese Application No. 201980041065.1 dated Dec. 29, 2023, 24 pp.
Kent et al., "Instrumentation to record evoked potentials for closed-loop control of deep brain stimulation", 2011 Annual International Conference of the IEEE Engineering in Medicine and Biology Society, IEEE, Aug. 6, 2012, pp. 6777-6780.
Notice of Allowance from U.S. Appl. No. 17/484,848 dated Mar. 11, 2024, 10 pp.
Response to Communication pursuant to Article 94(3) EPC dated Nov. 10, 2023, from counterpart European Application No. 19744916.8 filed Mar. 1, 2024, 7 pp.

* cited by examiner

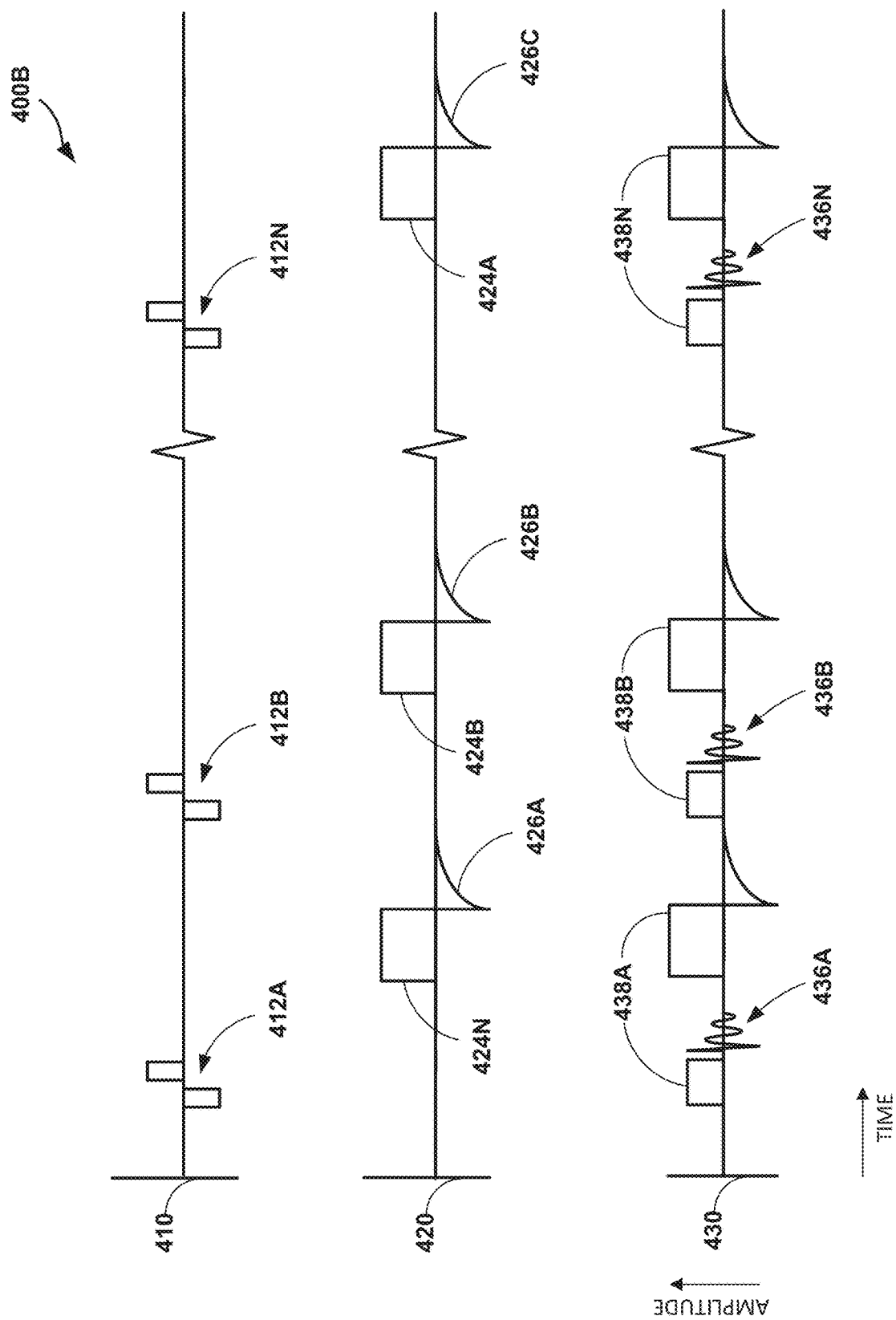

ECAP BASED CONTROL OF ELECTRICAL STIMULATION THERAPY

This application is a continuation of U.S. patent application Ser. No. 16/449,168 filed on Jun. 21, 2019 know U.S. Pat. No. 11,129,991, issued Sep. 28, 2021), which claims the benefit of U.S. Provisional Patent Application No. 62/688,223 filed on Jun. 21, 2018. The entire content of each of these applications is incorporated herein by reference.

TECHNICAL FIELD

This disclosure generally relates to electrical stimulation therapy, and more specifically, control of electrical stimulation therapy.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate to the spinal cord, proximate to the sacral nerve, within the brain, and proximate to peripheral nerves are often referred to as spinal cord stimulation (SCS), sacral neuromodulation (SNM), deep brain stimulation (DBS), and peripheral nerve stimulation (PNS), respectively.

Electrical stimulation therapy may be delivered by the medical device in a train of electrical stimulation pulses, and parameters that define the electrical stimulation pulses may include a frequency, an amplitude, a pulse width, and a pulse shape.

SUMMARY

Systems, devices, and techniques are described for controlling electrical stimulation therapy by sensing an evoked compound action potential (ECAP). In some examples, electrical stimulation pulses are delivered in the form of informed pulses and control pulses that are at least partially interleaved with each other. Control pulses are those stimulation pulses that are configured to elicit a detectable ECAP signal, e.g., ECAP test pulses. In some examples, control pulses may contribute to the therapy for a patient. In other examples, control pulses do not contribute to the therapy for the patient, e.g., non-therapeutic pulses. In this manner, control pulses may or may not be configured to elicit a therapeutic effect for the patient. Informed pulses are those stimulation pulses that are at least partially defined by one or more parameters based on the detectable ECAP signal elicited from one or more control pulses. In this manner, the informed pulses are "informed" by the ECAP signal detected from a control pulse. Informed pulses are also configured to provide a therapy to a patient, such as paresthesia that relieves pain symptoms.

A medical device (e.g., an implantable medical device) can deliver one or more control pulses to the patient via one or more leads, and the system may sense the resulting ECAP signal elicited by the control pulse(s)—all between consecutive informed pulses. For example, in response to determining that a characteristic of the ECAP signal (e.g., a voltage amplitude) has deviated from a target ECAP characteristic, the system may change one or more stimulation parameters of the next one or more informed pulses and/or control pulses to be delivered to the patient. For example, the system may increase or decrease a current amplitude of the informed pulses (and, in some examples, for control pulses) by a predetermined step size or based on a gain value representative of a growth curve for the patient. In this manner, the system may be configured to maintain a consistent volume of neural activation by adjusting the one or more stimulation parameters of the informed pulses and/or control pulses. As discussed herein, since ECAP signals elicited by informed pulses may not be detectable by the medical device, a value for one or more parameters of the informed pulses may be determined from a characteristic of the ECAP signal detected from a control pulse.

In some examples, control pulses may be non-therapeutic pulses, which are stimulation pulses having parameter values selected without the primary purpose of contributing to the therapy of the patient. In this example, one or more non-therapeutic pulses can be delivered to the patient, and the system may sense the resulting ECAP signal all between consecutive therapy pulses (e.g., informed pulses that are configured to contribute to the therapy of the patient). In response to determining that a characteristic of the ECAP signal (e.g., a voltage amplitude) has deviated from a target ECAP characteristic, the system may change one or more stimulation parameters of the next one or more therapy pulses to be delivered to the patient. For example, the system may increase or decrease a current amplitude of the therapy pulses by a predetermined step size or based on a gain value representative of a growth curve for the patient. In this manner, the system may be configured to maintain a consistent volume of neural activation by adjusting the one or more stimulation parameters of the therapy pulses.

In one example, a method includes delivering electrical stimulation therapy to a patient, the electrical stimulation therapy comprising a plurality of informed pulses at a predetermined pulse frequency over a period of time, wherein the plurality of informed pulses are at least partially defined by a first set of parameter values, delivering, over the period of time, a plurality of control pulses interleaved with at least some informed pulses of the plurality of informed pulses, wherein the plurality of control pulses are at least partially defined by a second set of parameter values different than the first set of parameter values, sensing, after one or more control pulses of the plurality of control pulses and prior to an immediately subsequent informed pulse of the plurality of informed pulses, a respective evoked compound action potential (ECAP), adjusting, based on at least one respective ECAP, one or more parameter values of the first set of parameter values that at least partially defines the plurality of informed pulses of the electrical stimulation therapy, and delivering the electrical stimulation therapy to the patient according to the adjusted one or more parameter values of the first set of parameter values.

In another example, a system includes stimulation generation circuitry configured to deliver electrical stimulation therapy to a patient, wherein the electrical stimulation therapy comprises a plurality of informed pulses at a predetermined pulse frequency over a period of time, and wherein the plurality of informed pulses are at least partially defined by a first set of parameter values, and deliver a plurality of control pulses over the period of time, wherein the plurality of control pulses are interleaved with at least some informed pulses of the plurality of informed pulses, and wherein the plurality of control pulses are at least partially defined by a second set of parameter values different than the first set of parameter values, and processing circuitry configured to receive a sensed respective evoked compound action potential (ECAP) after one or more control pulses of the plurality of control pulses and prior to a subsequent informed pulse of the plurality of informed pulses, adjust, based on at least one respective ECAP, one or more parameter values of the first set of parameter values that at least partially define the plurality of informed pulses of the electrical stimulation therapy, and deliver, via the stimulation generation circuitry, the electrical stimulation therapy to the patient according to the adjusted one or more parameter values of the first set of parameter values.

In another example, a computer-readable storage medium comprising instructions that, when executed, cause one or more processors to control delivery of electrical stimulation therapy to a patient, the electrical stimulation therapy comprising a plurality of informed pulses at a predetermined pulse frequency over a period of time, wherein the plurality of informed pulses are at least partially defined by a first set of parameter values, control, over the period of time, delivery of a plurality of control pulses interleaved with at least some informed pulses of the plurality of informed pulses, wherein the plurality of control pulses are at least partially defined by a second set of parameter values different than the first set of parameter values, receive, after one or more control pulses of the plurality of control pulses and prior to an immediately subsequent informed pulse of the plurality of informed pulses, a sensed respective evoked compound action potential (ECAP), adjust, based on at least one respective ECAP, one or more parameter values of the first set of parameter values that at least partially define the plurality of informed pulses of the electrical stimulation therapy, and control delivery of the electrical stimulation therapy to the patient according to the adjusted one or more parameter values of the first set of parameter values.

In another example, a method includes delivering a control stimulation pulse to a patient, the control stimulation pulse having a first pulse width, sensing an evoked compound action potential (ECAP) signal elicited by the control stimulation pulse, identifying a characteristic of the ECAP signal, determining, based on the characteristic of the ECAP signal and a gain value, a parameter value that at least partially defines an informed stimulation pulse from a plurality of informed pulses, wherein the plurality of informed pulses have a second pulse width longer than the first pulse width, and delivering the informed pulse according to the determined parameter value.

In another example, a system includes stimulation generation circuitry configured to deliver a control stimulation pulse to a patient, the control stimulation pulse having a first pulse width, and deliver an informed stimulation pulse from a plurality of informed pulses and according to a parameter value, wherein the plurality of informed pulses have a second pulse width longer than the first pulse width, and processing circuitry configured to receive a sensed evoked compound action potential (ECAP) signal elicited by the control stimulation pulse, identify a characteristic of the ECAP signal, and determine, based on the characteristic of the ECAP signal and a gain value, the parameter value that at least partially defines the informed pulse.

In another example, a computer-readable storage medium comprising instructions that, when executed, causes one or more processors to control delivery of a control stimulation pulse to a patient, the control stimulation pulse having a first pulse width, sense an evoked compound action potential (ECAP) signal elicited by the control stimulation pulse, identify a characteristic of the ECAP signal, determine, based on the characteristic of the ECAP signal and a gain value, a parameter value that at least partially defines an informed stimulation pulse from a plurality of informed pulses, wherein the plurality of informed pulses have a second pulse width longer than the first pulse width, and control delivery of the informed pulse according to the determined parameter value.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

FIG. 4B is a timing diagram illustrating an example of electrical stimulation pulses and respective sensed ECAPs according to the techniques of the disclosure.

DETAILED DESCRIPTION

Figure 1:
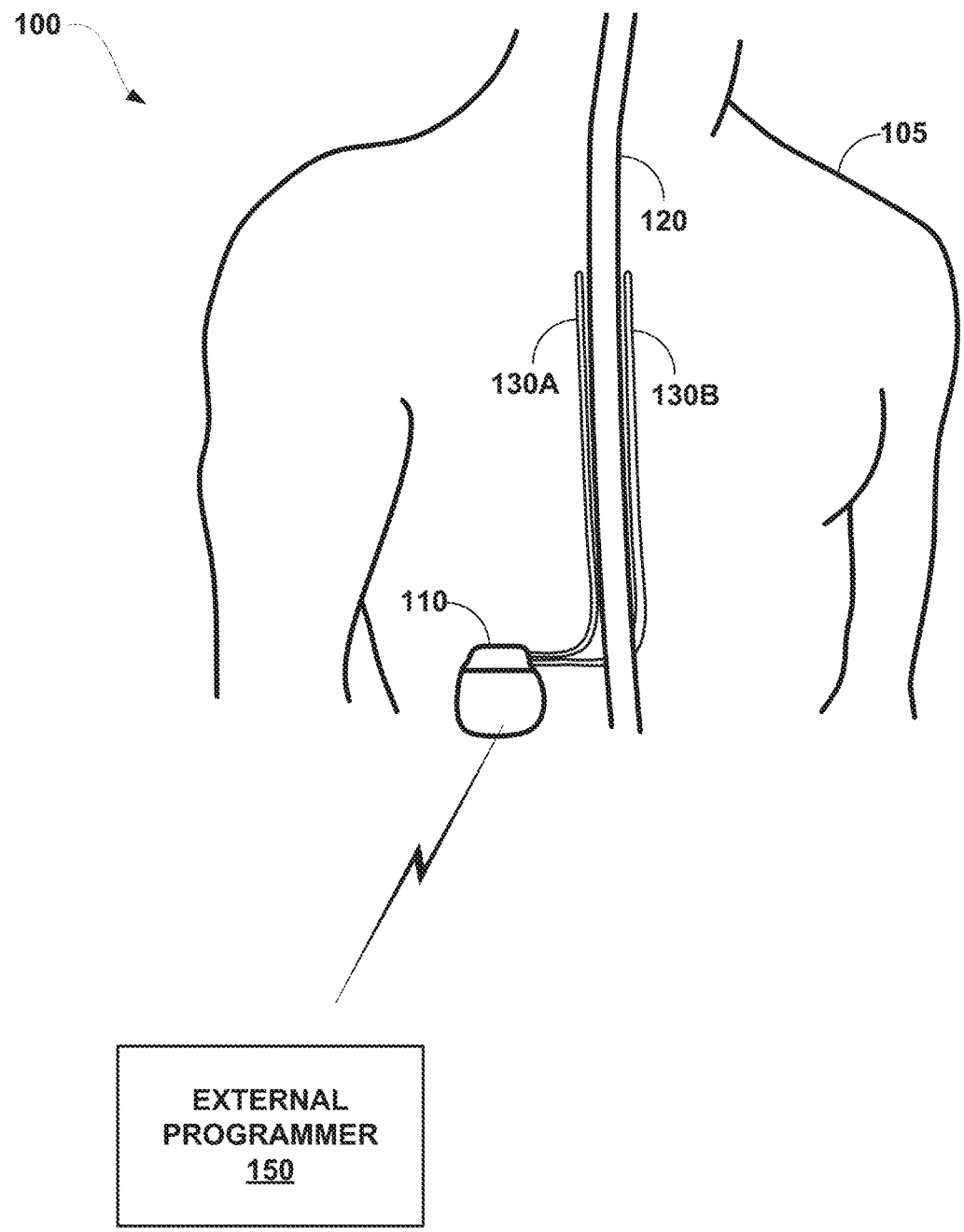
FIG. 1 is a conceptual diagram illustrating an example system that includes a medical device programmer and an implantable medical device (IMD) configured to deliver spinal cord stimulation (SCS) therapy according to the techniques of the disclosure.

The disclosure describes examples of medical devices, systems, and techniques for automatically adjusting electrical stimulation therapy delivered to a patient based on one or more characteristics of evoked compound action potentials (ECAPs) received by a medical device in response to control stimulation pulses delivered by the medical device. Electrical stimulation therapy is typically delivered to a target tissue (e.g., one or more nerves or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, muscle disorders, etc. However, as the patient moves, the distance between the electrodes and the target tissues changes. Since neural recruitment is a function of stimulation intensity and distance between the target tissue and the electrodes, movement of the electrode closer to the target tissue may result in increased perception by the patient (e.g., possible painful sensations), and movement of the electrode further from the target tissue may result in decreased efficacy of the therapy for the patient.

ECAPs are a measure of neural recruitment because each ECAP signal represents the superposition of electrical potentials generated from axons firing in response to an electrical stimulus (e.g., a stimulation pulse). Changes in a characteristic (e.g., an amplitude of a portion of the signal, an area under one or more peaks, frequency content, and/or maximum and/or minimum peak timing) of an ECAP signal occurs as a function of how many axons have been activated by the delivered stimulation pulse. A system can monitor changes in the characteristic of the ECAP signal and use that change in the characteristic to adjust one or more stimulation parameter of the informed pulses and/or control pulses delivered to the patient. For example, the system can reduce the intensity of stimulation pulses (e.g., reduce a current amplitude and/or pulse width) in response to detecting an increase in an amplitude of an ECAP signal. Nerve impulses detectable as the ECAP signal travel quickly along the nerve fiber after the delivered stimulation pulse first depolarizes the nerve. Therefore, if the stimulation pulse delivered by first electrodes has a pulse width that is too long, different electrodes configured to sense the ECAP will sense the stimulation pulse itself as an artifact that obscures the lower amplitude ECAP signal. However, the ECAP signal loses fidelity as the electrical potentials propagate from the electrical stimulus because different nerve fibers propagate electrical potentials at different speeds. Therefore, sensing the ECAP at a far distance from the stimulating electrodes may avoid the artifact caused by a stimulation pulse with a long pulse width, but the ECAP signal may lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient.

As described herein, a medical device may be configured to deliver a plurality of informed pulses and/or control pulses configured to provide a therapy to the patient based on one or more parameters of ECAP signals elicited by previously delivered control pulses. The medical device, in some cases, may deliver a plurality of informed pulses, which are configured to provide or at least contribute to a therapy to the patient based on one or more parameters of ECAP signals elicited by control pulses. In some examples, the control pulses may be configured to elicit ECAP signals without contributing to the therapy of the patient. However, in other examples, the control pulses may provide therapy to the patient either alone or in combination with the informed pulses. The control pulses may be interleaved with the delivery of the informed pulses. For example, the medical device may alternate the delivery of informed pulses with control pulses such that a control pulse is delivered, and an ECAP signal is sensed from the control pulses, between consecutive informed pulses. In some examples, multiple control pulses are delivered, and respective ECAP signals sensed, between the delivery of consecutive informed pulses. In some examples, multiple informed pulses will be delivered between consecutive control pulses. In any case, the informed pulses may be delivered according to a predetermined pulse frequency selected so that the informed pulses can produce or contribute to a therapeutic result for the patient. One or more control pulses are then delivered, and the respective ECAP signals sensed, within one or more time windows between consecutive informed pulses delivered according to the predetermined pulse frequency. The predetermined pulse frequency may be a single consistent frequency or a varied frequency that varies over time. The pulse width of the control pulses may be shorter than the pulse width of the informed pulses to enable the medical device to detect the ECAP signals elicited from the control pulses. Put another way, the longer pulse width of the informed pulses may prevent the resulting ECAP signals from being detected due to, for example, overlapping of the informed pulse with the ECAP signal. In this manner, a medical device can administer informed pulses from the medical device uninterrupted while ECAPs can be sensed from control pulses delivered during times at which the informed pulses are not being delivered.

In one example, the control pulses do not contribute to the therapy of the patient and may be referred to as non-therapeutic pulses. In this example, a medical device may be configured to deliver a plurality of therapy pulses (e.g., informed pulses) configured to provide a therapy to the patient and a plurality of non-therapeutic pulses configured to elicit a detectable ECAP signal without the primary purpose of providing a therapy to the patient. The non-therapy pulses may be interleaved with the delivery of the therapy pulses. For example, the medical device may alternate the delivery of therapy pulses with non-therapy pulses such that a non-therapy pulse is delivered, and an ECAP signal is sensed, between consecutive therapy pulses. In some examples, multiple non-therapy pulses are delivered, and respective ECAP signals sensed, between the delivery of consecutive therapy pulses. In some examples, multiple therapy pulses will be delivered between consecutive non-therapeutic pulses. In any case, the therapy pulses may be delivered according to a predetermined pulse frequency selected so that the therapy pulses can produce a therapeutic result for the patient. One or more non-therapeutic pulses are then delivered, and the respective ECAP signals sensed, within one or more time windows between consecutive therapy pulses delivered according to the predetermined pulse frequency. In this manner, a medical device can administer therapy pulses from the medical device uninterrupted while ECAPs are sensed from non-therapy pulses delivered during times at which the therapy pulses are not being delivered.

The system may adjust the value of one or more parameters that at least partially define the informed pulses in response to determining changes to one or more characteristics of the sensed ECAP signals received by the medical device. For instance, the medical device may measure an amplitude of the ECAP signal elicited by a control pulse and compare it to a target ECAP amplitude previously identified as appropriate for the patient. If the amplitude of the ECAP signal (e.g. a voltage amplitude of one or more peaks in the ECAP signal) is greater than a target ECAP amplitude, then the intensity of the control pulses may be too high because the stimulation electrodes have moved closer to the nerves. The medical device may responsively reduce the intensity (e.g., current amplitude, pulse width, pulse frequency, slew rate, or any combination thereof) of the informed pulses. Conversely, if the amplitude of the ECAP signal is less than the target ECAP amplitude, then the intensity of the control pulses may not be strong enough because the stimulation electrodes have moved farther from the nerves. The medical device may responsively increase the intensity of the informed pulses. In this manner, the medical device may monitor the ECAP signal elicited from the control pulses to adjust one or more parameters of informed pulses to maintain a volume of neural activation that provides efficacious therapy for the patient.

The pulse width of the control pulses may be shorter than the pulse width of the informed pulses to reduce or prevent a sensed electrical artifact from control pulses from obscuring the ECAP signals (put another way, the pulse width of the informed pulses may be longer than the pulse width of the control pulses). For example, the control pulses may be less than approximately 300 microseconds (μs). In one example, the control pulse may be a bi-phasic pulse having a positive phase of approximately 100 μs and a negative phase of approximately 100 μs separated by an interphase interval of approximately 30 μs. In this manner, stimulation electrodes at one end of a lead may deliver the control pulse and electrodes at the other end of the same lead may sense the ECAP signal without, or with minimal, interference from the control pulse itself.

In one example, a system may adjust one or more parameters of informed pulses based on sensed ECAP signals. The medical device may determine a representative amplitude of at least one respective ECAP signal. The medical device may then compare the representative amplitude to a target ECAP characteristic (e.g., a target ECAP amplitude or other characteristics such as frequency content, area under one or more peaks, or the timing of one or more peaks) and a target ECAP adjustment window. The target ECAP adjustment window may be a range of amplitudes around the target ECAP amplitude, including an upper-bound and a lower-bound. In some examples, the target ECAP adjustment window may be defined by the target ECAP characteristic plus and minus a variance so that adjustments are not made to the one or more parameters of the informed pulses for minor oscillations in the ECAP signal. In other words, the target ECAP characteristic plus the variance may be the upper-bound of the target ECAP adjustment window, and the target ECAP characteristic minus the variance may be the lower-bound of the target ECAP adjustment window. The variance may be the same or different above and below the target ECAP characteristic. If the representative amplitude of the at least one respective ECAP is greater than the upper-bound of the target ECAP adjustment window, then the medical device may be configured to decrease the amplitude of subsequent informed pulses and the control pulses. The control pulses may also be adjusted in order to determine if further adjustments are needed based on subsequently detected ECAP signals. If the representative amplitude of the at least one respective ECAP is lower than the lower-bound of the target ECAP adjustment window, then the medical device may be configured to increase the amplitude of the informed pulses and the control pulses following the at least one respective ECAP. The amount that the amplitude of the informed pulses and control pulses is changed may be a predetermined amplitude step size or a predetermined percentage based on the detected change in the representative amplitude of the ECAP signal. In this manner, the feedback loop may take more than one iteration to achieve the target ECAP amplitude once again.

In another example, the medical device may employ a dynamic feedback loop. A growth curve may be determined for the patient that is determined based on the slope of the relationship between detected values of a characteristic of ECAP signals for respective different stimulation pulse amplitudes. Therefore, the medical device may determine a difference between the target ECAP characteristic value (e.g., an amplitude value, area under one or more peaks, frequency content, or maximum and/or minimum peak timing) and a measured ECAP value and multiply the difference by the gain value. The resulting value can then be used to increase or decrease the previous parameter value that defined the control pulse that resulted in the measured ECAP value. The gain value can also be used to similarly adjust the parameter values of the informed pulses. By employing the gain value, the system may be able to respond quickly to large ECAP signal variations and reset the informed pulses and control pulses to the target ECAP. This process may reduce the number of informed pulses that produce less effective therapy resulting from electrode-to-tissue distance changes during patient movement.

Informed pulses and control pulses are generally described herein as different stimulation pulses reflective of different types of electrical stimulation. However, the different types of electrical stimulation, and their respective pulses, may be described with different attributes. For example, a first type of electrical stimulation may include first pulses configured to primarily contribute to a therapy for a patient. The first pulses of this first type of electrical stimulation may also have one or more characteristics (e.g., a pulse width) that prevent or reduce the ability of the system to detect ECAP signals elicited from the first pulses of the first type of electrical stimulation because an artifact representative of the first pulses themselves overlaps with and obscures at least a portion of the respective elicited ECAP signal. A second type of electrical stimulation may include second pulses defined by one or more parameter values selected to elicit ECAP signals that are sensed and detectable by the system. The second pulses may thus be referred to as "control pulses," "sense pulses," or "test pulses" since the second pulses are configured to elicit a detectable ECAP signal. For example, the second pulses of the second type of electrical stimulation may improve the detectability of the ECAP signal such as to not generate an artifact (or reduce the presence of an artifact) that obscures the ECAP signals or otherwise prevents or reduces the ability of the system to detect the ECAP signal from each of the second pulses. In addition, the second pulses may be defined by parameter values selected to elicit an ECAP signal that is used to at least modify one or more parameter values of the first pulses (e.g., informed pulses) of the first type of electrical stimulation. The first pulses may thus differ from the second pulses by at least one parameter (e.g., current and/or voltage amplitude, pulse width, and/or frequency). As discussed herein, in some examples the second pulses have a pulse width shorter than the pulse width of the first pulses. The first pulses may be at least partially interleaved with at least some of the second pulses. For example, the system may alternate delivery of one first pulse with delivery of one second pulse. In another example, the number of first pulses may differ from the number of second pulses by a ratio or percentage. The ratio could be 1:1 when the first and second pulses are fully interleaved. The ratio could be 10:1 first pulses to second pulses in examples in which the second pulses are delivered less frequently than the first pulses. In other examples, the ratio could be 1:4 first pulses to second pulses when the second pulses, and respective sensed ECAP signals) occur more frequently than the first pulses. The second pulses may or may not contribute to a therapy or sensation perceived by the patient, but the primary purpose of the second pulses is to elicit respective ECAP signals that are detectable by the system separate from any sensed artifacts representative of the second pulses themselves. Since the ECAP signals elicited by the second pulses are detectable, the system may use the ECAP signals from one or more of the second pulses in order to "inform" or otherwise adjust one or more parameter values that at least partially defines the first pulses (e.g., informed pulses).

Although electrical stimulation is generally described herein in the form of electrical stimulation pulses, electrical stimulation may be delivered in non-pulse form in other examples. For example, electrical stimulation may be delivered as a signal having various waveform shapes, frequencies, and amplitudes. Therefore, electrical stimulation in the form of a non-pulse signal may be a continuous signal than may have a sinusoidal waveform or other continuous waveform.

FIG. 1 is a conceptual diagram illustrating example system 100 that includes implantable medical device (IMD) 110 configured to deliver electrical stimulation therapy to patient 105. In the example shown in FIG. 1, IMD 110 is configured to deliver spinal cord stimulation (SCS) therapy according to the techniques of the disclosure. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively, "leads 130"), e.g., for relief of chronic pain or other symptoms. In other examples, IMD 110 may be coupled to a single lead carrying multiple electrodes or more than two leads each carrying multiple electrodes. In addition to electrical stimulation therapy, IMD 110 may also be configured to generate and deliver control pulses configured to elicit ECAP signals that may or may not contribute to the therapy of informed pulses. As discussed herein, the control pulses may be non-therapeutic in some examples. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, PAD 110 is leadless.

IMD 110 may be constructed of any polymer, metal, or composite material sufficient to house the components of IMD 110 (e.g., components illustrated in FIG. 2A) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 may be selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead of leads 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, leads 130 may include a lead extension or other segments that may aid in implantation or positioning of leads 130. In some other examples, IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of leads 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead. In other examples, one or more of leads 130 are linear leads having 8 ring electrodes along the axial length of the lead. In another example, the electrodes are segmented rings arranged in a linear fashion along the axial length of the lead and at the periphery of the lead.

The stimulation parameter of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, and voltage or current amplitude, pulse frequency, pulse width, pulse shape of stimulation delivered by the electrodes. These stimulation parameters of informed pulses are typically predetermined parameter values determined prior to delivery of the informed pulses. However, in some examples, system 100 may change one or more parameter values automatically based on one or more factors or based on user input.

In addition to stimulation informed pulses, an ECAP test stimulation program may define stimulation parameter values that define control pulses delivered by IMD 110 through at least some of the electrodes of leads 130. These stimulation parameter values may include information identifying which electrodes have been selected for delivery of control pulses, the polarities of the selected electrodes, i.e., the electrode combination for the program, and voltage or current amplitude, pulse frequency, pulse width, and pulse shape of stimulation delivered by the electrodes. The stimulation signals (e.g., one or more stimulation pulses or a continuous stimulation waveform) defined by the parameters of each ECAP test stimulation program are configured to evoke a compound action potential from nerves. In some examples, the ECAP test stimulation program may define when the control pulses are to be delivered to the patient based on the frequency and/or pulse width of the informed pulses. However, the stimulation defined by each ECAP test stimulation program are not intended to provide or contribute to therapy for the patient. In an example where the control pulses contribute to or provide therapy for the patient, the ECAP test stimulation program may also be used in place of, or be the same as, a therapy stimulation program.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, leads 130 may include one or more sensors configured to allow IMD 110 to monitor one or more parameters of patient 105, such as patient activity, pressure, temperature, or other characteristics. The one or more sensors may be provided in addition to, or in place of, therapy delivery by leads 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate to spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 generates and delivers electrical stimulation therapy to a target stimulation site within patient 105 via the electrodes of leads 130 to patient 105 according to one or more therapy stimulation programs. A therapy stimulation program defines values for one or more parameters that define an aspect of the therapy delivered by IMD 110 according to that program. For example, a therapy stimulation program that controls delivery of stimulation by IMD 110 in the form of pulses may define values for voltage or current pulse amplitude, pulse width, and pulse rate (e.g., pulse frequency) for stimulation pulses delivered by IMD 110 according to that program. A therapy stimulation program may define control pulses and/or informed pulses when these pulses are configured to contribute to the therapeutic effect (e.g., paresthesia, pain blocking, etc.) for the patient.

Furthermore, IMD 110 is configured to deliver control stimulation to patient 105 via a combination of electrodes of leads 130, alone or in combination with an electrode carried by or defined by an outer housing of IMD 110. The tissue targeted by the control stimulation may be the same tissue targeted by the electrical stimulation therapy, but IMD 110 may deliver control pulses via the same, at least some of the same, or different electrodes, and intended to elicit a detectable ECAP signal. This control stimulation may (e.g., therapeutic stimulation) or may not (e.g., non-therapeutic stimulation) contribute to a therapeutic effect for the patient. Since control pulses can be delivered in an interleaved manner with informed pulses, a clinician and/or user may select any desired electrode combination for informed pulses. Like the electrical stimulation therapy, the control stimulation may be in the form of electrical stimulation pulses or continuous waveforms. In one example, each control pulse may include a balanced, bi-phasic square pulse that employs an active recharge phase. However, in other examples, the control pulses may include a monophasic pulse followed by a passive recharge phase. In other examples, a control pulse may include an imbalanced bi-phasic portion and a passive recharge portion. Although not necessary, a bi-phasic control pulse may include an interphase interval between the positive and negative phase to promote propagation of the nerve impulse in response to the first phase of the bi-phasic pulse. The control stimulation may be delivered without interrupting the delivery of the electrical stimulation informed pulses, such as during the window between consecutive informed pulses. The control pulses may elicit an ECAP signal from the tissue, and IMD 110 may sense the ECAP signal via two or more electrodes on leads 130. In cases where the control pulses are applied to spinal cord 120, the signal may be sensed by IMD 110 from spinal cord 120. As discussed herein, the control stimulation may contribute, alone or in part, to the therapeutic effect received by the patient. In other words, control pulses may be delivered to provide therapy without any additional informed pulses in some examples. In examples in which the control pulses alone can provide therapy to the patient, the control stimulation may be the therapy stimulation for that patient.

IMD 110 delivers control stimulation to a target stimulation site within patient 105 via the electrodes of leads 130 according to one or more ECAP test stimulation programs. The one or more ECAP test stimulation programs may be stored in a memory of IMD 110. Each ECAP test program of the one or more ECAP test stimulation programs includes values for one or more parameters that define an aspect of the control stimulation delivered by IMD 110 according to that program, such as current or voltage amplitude, pulse width, pulse frequency, electrode combination, and, in some examples timing based on informed pulses to be delivered to patient 105. In some examples, IMD 110 delivers control stimulation to patient 105 according to multiple ECAP test stimulation programs.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from programmer 150 to control electrical stimulation therapy (e.g., informed pulses, and in some examples control pulses) and control stimulation (e.g., control pulses). For example, external programmer 150 may transmit therapy stimulation programs, ECAP test stimulation programs, stimulation parameter adjustments, therapy stimulation program selections, ECAP test program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and programmer 150 may communicate via wireless communication using any techniques known in the art. Examples of communication techniques may include, for example, radiofrequency (RF) telemetry and inductive coupling, but other techniques are also contemplated. In some examples, programmer 150 may include a communication head that may be placed proximate to the patient's body near the IMD 110 implant site to improve the quality or security of communication between IMD 110 and programmer 150. Communication between programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 may modify therapy stimulation programs as therapy needs of patient 105 evolve over time. For example, the modification of the therapy stimulation programs may cause the adjustment of at least one parameter of the plurality of informed pulses. When patient 105 receives the same therapy for an extended period, the efficacy of the therapy may be reduced. In some cases, parameters of the plurality of informed pulses may be automatically updated.

In this disclosure, efficacy of electrical stimulation therapy may be indicated by one or more characteristics (e.g. an amplitude of or between one or more peaks or an area under the curve of one or more peaks) of an action potential that is evoked by a stimulation pulse delivered by IMD 110 (i.e., a characteristic of the ECAP signal). Electrical stimulation therapy delivery by leads 130 of IMD 110 may cause neurons within the target tissue to evoke a compound action potential that travels up and down the target tissue, eventually arriving at sensing electrodes of IMD 110. Furthermore, control stimulation may also elicit at least one ECAP, and ECAPs responsive to control stimulation may also be a surrogate for the effectiveness of the therapy. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters may contribute to an intensity of the electrical stimulation. In addition, a characteristic of the ECAP signal (e.g., an amplitude) may change based on the distance between the stimulation electrodes and the nerves subject to the electrical field produced by the delivered control pulses.

In one example, each informed pulse may have a pulse width greater than approximately 300 μs, such as between approximately 300 μs and 1000 μs (i.e., 1 millisecond) in some examples. At these pulse widths, IMD 110 may not sufficiently detect an ECAP signal because the informed pulse is also detected as an artifact that obscures the ECAP signal. If ECAPs are not adequately recorded, then ECAPs arriving at IMD 110 cannot be compared to the target ECAP characteristic (e.g. a target ECAP amplitude), and electrical therapy stimulation cannot be altered according to responsive ECAPs. When informed pulses have these longer pulse widths, IMD 110 may deliver control stimulation in the form of control pulses. The control pulses may have pulse widths of less than approximately 300 μs, such as a bi-phasic pulse with each phase having a duration of approximately 100 μs. Since the control pulses may have shorter pulse widths than the informed pulses, the ECAP signal may be sensed and identified following each control pulse and used to inform IMD 110 about any changes that should be made to the informed pulses (and control pulses in some examples). In some examples, at least some informed pulses may have pulse widths less than approximately 300 µs. In such examples, control pulses interleaved with the informed pulses may have pulse widths shorter than the pulse widths of informed pulses. In other examples, a control pulse may have a pulse width greater than the pulse width of the informed pulse. In general, the term "pulse width" refers to the collective duration of every phase, and interphase interval when appropriate, of a single pulse. A single pulse may include a single phase in some examples (i.e., a monophasic pulse) or two or more phases in other examples (e.g., a bi-phasic pulse or a tri-phasic pulse). The pulse width defines a period of time beginning with a start time of a first phase of the pulse and concluding with an end time of a last phase of the pulse (e.g., a biphasic pulse having a positive phase lasting 100 µs, a negative phase lasting 100 µs, and an interphase interval lasting 30 µs defines a pulse width of 230 µs).

As described, the example techniques for adjusting stimulation parameter values for informed pulses are based on comparing the value of a characteristic of a measured ECAP signal to a target ECAP characteristic value. During delivery of control pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of the patient 105. Examples of the one or more sensors include one or more sensors configured to measure a compound action potential of the patient 105, or a physiological effect indicative of a compound action potential. For example, to measure a physiological effect of a compound action potential, the one or more sensors may be an accelerometer, a pressure sensor, a bending sensor, a sensor configured to detect a posture of patient 105, or a sensor configured to detect a respiratory function of patient 105. However, in other examples, external programmer 150 receives a signal indicating a compound action potential in the target tissue of patient 105 and transmits a notification to IMD 110.

In the example of FIG. 1, IMD 110 described as performing a plurality of processing and computing functions. However, external programmer 150 instead may perform one, several, or all of these functions. In this alternative example, PAD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value, and in response to the comparison, external programmer 150 may instruct IMD 110 to adjust one or more parameter that defines the electrical stimulation informed pulses and, in some examples, control pulses, delivered to patient 105.

In the example techniques described in this disclosure, the control stimulation parameters and the target ECAP characteristic values may be initially set at the clinic but may be set and/or adjusted at home by patient 105. Once the target ECAP characteristic values are set, the example techniques allow for automatic adjustment of informed pulse parameters to maintain consistent volume of neural activation and consistent perception of therapy for the patient when the electrode-to-neuron distance changes. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. IMD 110 may perform these changes without intervention by a physician or patient 105.

In some examples, the system may change the target ECAP characteristic value over a period of time. The system may be programmed to change the target ECAP characteristic in order to adjust the intensity of informed pulses to provide varying sensations to the patient (e.g., increase or decrease the volume of neural activation). In one example, a system may be programmed to oscillate a target ECAP characteristic value between a maximum target ECAP characteristic value and a minimum target ECAP characteristic value at a predetermined frequency to provide a sensation to the patient that may be perceived as a wave or other sensation that may provide therapeutic relief for the patient. The maximum target ECAP characteristic value, the minimum target ECAP characteristic value, and the predetermined frequency may be stored in the memory of IMD 110 and may be updated in response to a signal from external programmer 150 (e.g., a user request to change the values stored in the memory of IMD 110). In other examples, the target ECAP characteristic value may be programed to steadily increase or steadily decrease to a baseline target ECAP characteristic value over a period of time. In other examples, external programmer 150 may program the target ECAP characteristic value to automatically change over time according to other predetermined functions or patterns. In other words, the target ECAP characteristic value may be programmed to change incrementally by a predetermined amount or predetermined percentage, the predetermined amount or percentage being selected according to a predetermined function (e.g., sinusoid function, ramp function, exponential function, logarithmic function, or the like). Increments in which the target ECAP characteristic value is changed may be changed for every certain number of pulses or a certain unit of time. Although the system may change the target ECAP characteristic value, received ECAP signals may still be used by the system to adjust one or more parameter values of the informed pulses and/or control pulses in order to meet the target ECAP characteristic value.

Figure 2A:
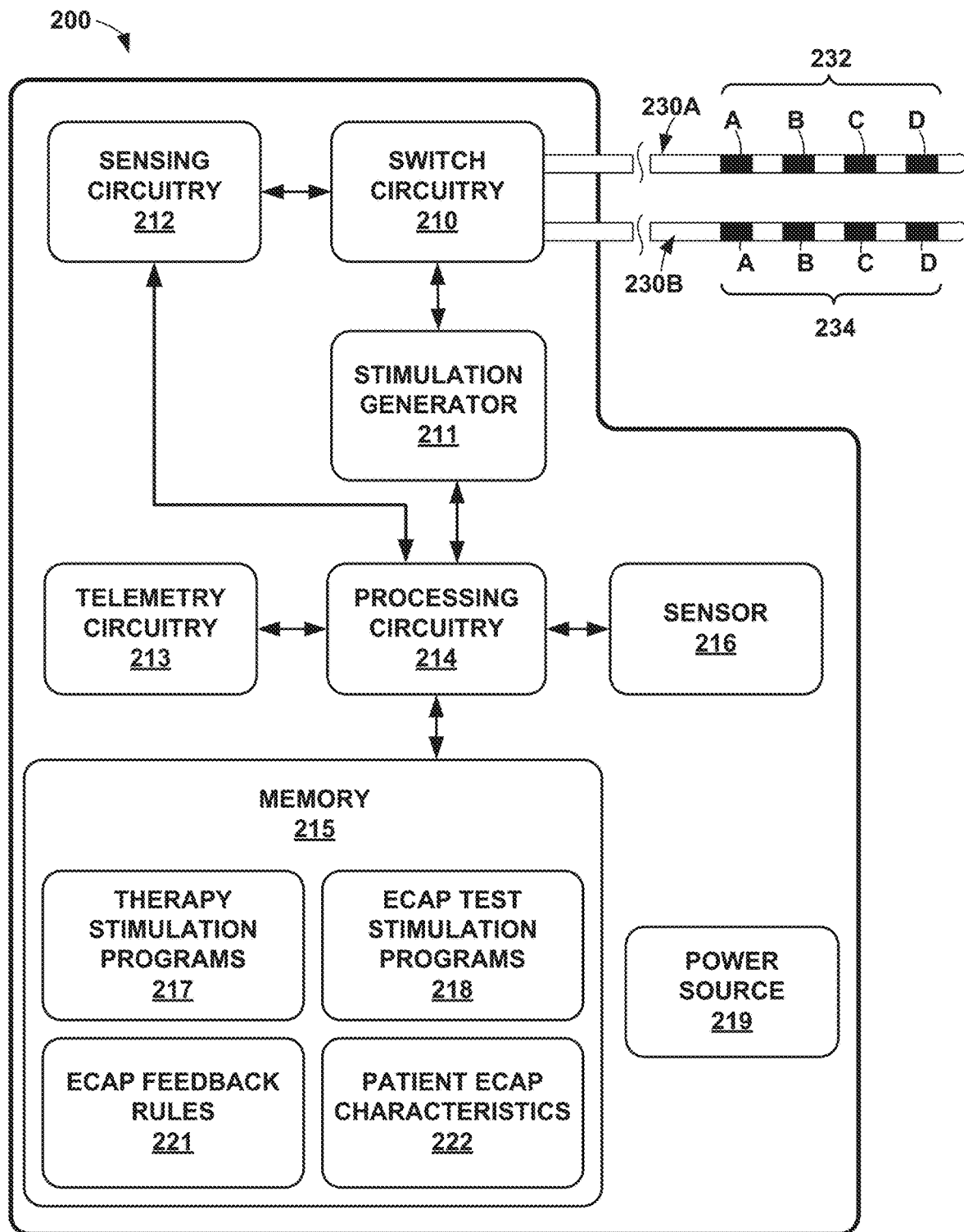
FIG. 2A is a block diagram of the example IMD of FIG. 1.

FIG. 2A is a block diagram of IMD 200. IMD 200 may be an example of IMD 110 of FIG. 1. In the example shown in FIG. 2A, IMD 200 includes processing circuitry 214, memory 215, stimulation generator 211, sensing circuitry 212, telemetry circuitry 213, sensor 216, and power source 219. Each of these circuits may be or include programmable or fixed function circuitry configured to perform the functions attributed to respective circuitry. For example, processing circuitry 214 may include fixed-function or programmable circuitry, stimulation generator 211 may include circuitry configured to generate stimulation signals such as pulses or continuous waveforms on one or more channels, sensing circuitry 212 may include sensing circuitry for sensing signals, and telemetry circuitry 213 may include telemetry circuitry for transmission and reception of signals. Memory 215 may store computer-readable instructions that, when executed by processing circuitry 214, cause IMD 200 to perform various functions. Memory 215 may be a storage device or other non-transitory medium.

In the example shown in FIG. 2A, memory 215 stores therapy stimulation programs 217 and ECAP test stimulation programs 218 in separate memories within memory 215 or separate areas within memory 215. Memory 215 also stores target ECAP feedback rules 221 and patient ECAP characteristics 222. Each stored therapy stimulation program 217 defines values for a set of electrical stimulation parameters (e.g., a parameter set or set of parameter values), such as a stimulation electrode combination, electrode polarity, current or voltage amplitude, pulse width, pulse rate, and pulse shape. Each stored ECAP test stimulation programs 218 defines values for a set of electrical stimulation parameters (e.g., a control stimulation parameter set), such as a stimulation electrode combination, electrode polarity, current or voltage amplitude, pulse width, pulse rate, and pulse shape. ECAP test stimulation programs 218 may also have additional information such as instructions regarding when to deliver control pulses based on the pulse width and/or frequency of the informed pulses defined in therapy stimulation programs 217.

Accordingly, in some examples, stimulation generator 211 generates electrical stimulation signals in accordance with the electrical stimulation parameters noted above. Other ranges of parameter values may also be useful and may depend on the target stimulation site within patient 105. While stimulation pulses are described, stimulation signals may be of any form, such as continuous-time signals (e.g., sine waves) or the like. Switch circuitry 210 may include one or more switch arrays, one or more multiplexers, one or more switches (e.g., a switch matrix or other collection of switches), or other electrical circuitry configured to direct stimulation signals from stimulation generator 211 to one or more of electrodes 232, 234, or directed sensed signals from one or more of electrodes 232, 234 to sensing circuitry 212. In other examples, stimulation generator 211 and/or sensing circuitry 212 may include sensing circuitry to direct signals to and/or from one or more of electrodes 232, 234, which may or may not also include switch circuitry 210.

Processing circuitry 214 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 214 herein may be embodied as firmware, hardware, software or any combination thereof. Processing circuitry 214 controls stimulation generator 211 to generate stimulation signals according to therapy stimulation programs 217 and ECAP test stimulation programs 218 stored in memory 215 to apply stimulation parameter values specified by one or more of programs, such as amplitude, pulse width, pulse rate, and pulse shape of each of the stimulation signals.

In the example shown in FIG. 2A, the set of electrodes 232 includes electrodes 232A, 232B, 232C, and 232D, and the set of electrodes 234 includes electrodes 234A, 234B, 234C, and 234D. In other examples, a single lead may include all eight electrodes 232 and 234 along a single axial length of the lead. Processing circuitry 214 also controls stimulation generator 211 to generate and apply the stimulation signals to selected combinations of electrodes 232, 234. In some examples, stimulation generator 211 includes a switch circuit (instead of, or in addition to, switch circuitry 210) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2A) with selected electrodes 232, 234.

In other examples, however, stimulation generator 211 does not include a switch circuit and switch circuitry 212 does not interface between stimulation generator 211 and electrodes 232, 234. In these examples, stimulation generator 211 comprises a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generator 211, e.g., via switch circuitry 210 and/or switching circuitry of the stimulation generator 211, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 212 is incorporated into a common housing with stimulation generator 211 and processing circuitry 214 in FIG. 2A, in other examples, sensing circuitry 212 may be in a separate housing from IMD 200 and may communicate with processing circuitry 214 via wired or wireless communication techniques.

In some examples, one or more of electrodes 232 and 234 may be suitable for sensing the ECAPs. For instance, electrodes 232 and 234 may sense the voltage amplitude of a portion of the ECAP signals, where the sensed voltage amplitude is a characteristic the ECAP signal.

Sensor 216 may include one or more sensing elements that sense values of a respective patient parameter. As described, electrodes 232 and 234 may be the electrodes that sense the parameter value of the ECAP. Sensor 216 may include one or more accelerometers, optical sensors, chemical sensors, temperature sensors, pressure sensors, or any other types of sensors. Sensor 216 may output patient parameter values that may be used as feedback to control delivery of therapy. For example, sensor 216 may indicate patient activity, and processing circuitry 214 may increase the frequency of control pulses and ECAP sensing in response to detecting increased patient activity. In one example, processing circuitry 214 may initiate control pulses and corresponding ECAP sensing in response to a signal from sensor 216 indicating that patient activity has exceeded an activity threshold. Conversely, processing circuitry 214 may decrease the frequency of control pulses and ECAP sensing in response to detecting decreased patient activity. For example, in response to sensor 216 no longer indicating that the sensed patient activity exceeds a threshold, processing circuitry 214 may suspend or stop delivery of control pulses and ECAP sensing. In this manner, processing circuitry 214 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry circuitry 213, for example. In some examples, one or more of these remote sensors may be external to patient (e.g., carried on the external surface of the skin, attached to clothing, or otherwise positioned external to the patient). In some examples, signals from sensor 216 may indicate a position or body state (e.g., sleeping, awake, sitting, standing, or the like), and processing circuitry 214 may select target ECAP characteristic values according to the indicated position or body state.

Telemetry circuitry 213 supports wireless communication between IMD 200 and an external programmer (not shown in FIG. 2A) or another computing device under the control of processing circuitry 214. Processing circuitry 214 of IMD 200 may receive, as updates to programs, values for various stimulation parameters such as amplitude and electrode combination, from the external programmer via telemetry circuitry 213. Updates to the therapy stimulation programs 217 and ECAP test stimulation programs 218 may be stored within memory 215. Telemetry circuitry 213 in IMD 200, as well as telemetry circuits in other devices and systems described herein, such as the external programmer, may accomplish communication by radiofrequency (RF) communication techniques. In addition, telemetry circuitry 213 may communicate with an external medical device programmer (not shown in FIG. 2A) via proximal inductive interaction of IMD 200 with the external programmer. The external programmer may be one example of external programmer 150 of FIG. 1. Accordingly, telemetry circuitry 213 may send information to the external programmer on a continuous basis, at periodic intervals, or upon request from IMD 110 or the external programmer.

Power source 219 delivers operating power to various components of IMD 200. Power source 219 may include a rechargeable or non-rechargeable battery and a power generation circuit to produce the operating power. Recharging may be accomplished through proximal inductive interaction between an external charger and an inductive charging coil within IMD 200. In other examples, traditional primary cell batteries may be used.

According to the techniques of the disclosure, stimulation generator 211 of IMD 200 receives, via telemetry circuitry 213, instructions to deliver electrical stimulation therapy according to therapy stimulation programs 217 to a target tissue site of the spinal cord of the patient via a plurality of electrode combinations of electrodes 232, 234 of leads 230 and/or a housing of IMD 200. Stimulation generator 211 may receive, via telemetry circuitry 213, user instructions to deliver control stimulation to the patient according to ECAP test stimulation programs 218. Each pulse of a plurality of control pulses may elicit an ECAP that is sensed by sensing circuitry 212 via some of electrodes 232 and 234. ECAP test stimulation programs 218 may instruct stimulation generator 211 to deliver a plurality of control pulses interleaved with at least some of the plurality of informed pulses. Processing circuitry 214 may receive, via an electrical signal sensed by sensing circuitry 212, information indicative of an ECAP signal (e.g., a numerical value indicating a characteristic of the ECAP in electrical units such as voltage or power) produced in response to the control stimulation. Therapy stimulation programs 217 may be updated according to the ECAPs recorded at sensing circuitry 212 according to the following techniques.

In one example, the plurality of informed pulses each have a pulse width of greater than approximately 300 µs and less than approximately 2000 µs (i.e., 2 milliseconds). In some examples, the informed pulse width is greater than approximately 300 µs and less than approximately 800 µs. In another example, the informed pulse width is greater than approximately 300 µs and less than approximately 500 µs. In one example, informed pulses have a pulse width of approximately 450 µs and a pulse frequency of approximately 60 Hertz. Amplitude (current and/or voltage) for the informed pulses may be between approximately 0.5 mA (or volts) and approximately 10 mA (or volts), although amplitude may be lower or greater in other examples. In some examples, the system may deliver informed pulses from two or more stimulation programs such that the informed pulses from one stimulation program have at least one different parameter value than the informed pulses from another stimulation program.

Each control pulse of the plurality of control pulses may have a pulse width of less than approximately 300 µs. In one example, each control pulse of the plurality of control pulses may be a bi-phasic pulse with a positive phase having a width of approximately 100 µs, a negative phase having a width of approximately 100 µs, and an interphase interval having a width of approximately 30 µs. In some examples, the positive phase and negative phase may each be 90 µs or 120 µs in other examples. In other examples, the control pulses may each have a pulse width of approximately 60 µs or smaller. Due to the relatively long pulse widths of the plurality of informed pulses, sensing circuitry 212 may be incapable of adequately recording an ECAP signals elicited from an informed pulse because the informed pulse itself will occur during the ECAP signal and obscure the ECAP signal. However, stimulation pulses with pulse widths less than approximately 300 microseconds, such as the plurality of control pulses, may be suited to elicit an ECAP which can be sensed after the control pulse is completed at sensing circuitry 212 via two or more of electrodes 232 and 234. In some examples, the control pulses may be non-therapeutic pulses in that the control pulses do not contribute to therapy for the patient. In other examples, the control pulses may fully provide or partially contribute to the therapy received by the patient by reducing or eliminating symptoms and/or a condition of the patient.

Control pulses delivered for the purpose of eliciting detectable ECAP signals may have a current amplitude between approximately 6 mA and 12 mA in some examples, but higher or lower amplitudes may be used in other examples. The frequency of the control pulses may be between approximately 50 Hertz and 400 Hertz in some examples, which may match the predetermined pulse frequency of the informed pulses when one control pulse is delivered for each therapeutic pulse. The predetermined pulse frequency may be a single frequency or a varied frequency over time (e.g., the interpulse interval may change over time according to predetermined pattern, formula, or schedule). In some examples, the system may change the predetermined pulse frequency based on patient input or a sensed parameter such as patient posture or activity. Such a relationship may be present when the control pulses are fully interleaved (e.g., alternating) with the informed pulses. However, the frequency of the control pulses may be delivered at a higher frequency than then informed pulses when two or more control pulses are delivered between consecutive informed pulses. In other examples, the frequency of the control pulses may be delivered at a lower frequency than the informed pulses when at least some informed pulses are delivered without a control pulse delivered between them. The frequency of the control pulses may be delivered at a frequency that varies over time if the system is configured to adjust control pulse delivery, and the resulting ECAP sensing, based on other factors such as patient activity.

In one example, the predetermined pulse frequency of the plurality of informed pulses may be less than approximately 400 Hertz. In some examples, the predetermined pulse frequency of the plurality of informed pulses may be between approximately 50 Hertz and 70 Hertz. In one example, the predetermined pulse frequency of the plurality of informed pulses may be approximately 60 Hertz. However, the informed pulses may have frequencies greater than 400 Hertz or less than 50 Hertz in other examples. In some examples, the predetermined pulse frequency of the informed pulses may be a single frequency or a frequency that varies over time. In addition, the informed pulses may be delivered in bursts of pulses, with interburst frequencies of the pulses being low enough such that a control pulse and sensed ECAP can still fit within the window between consecutive informed pulses delivered within the burst of informed pulses.

Since each informed pulse of the plurality of informed pulses may be sensed as an artifact that covers, or obscures, the sensing of at least one ECAP, the plurality of control pulses may be delivered to the patient during a plurality of time events. For example, a time event (e.g., a window) of the plurality of time events may be a time (e.g., a window) between consecutive informed pulses of the plurality of informed pulses at the predetermined pulse frequency. One or more control pulses of the plurality of control pulses may be delivered to the patient during each time event. Consequently, the control pulses may be interleaved with at least some of the informed pulses such that the plurality of control pulses are delivered to the patient while informed pulses are not delivered. In one example, an ECAP elicited from to a control pulse delivered during a time event may be recorded by sensing circuitry 212 during the same time event. In another example, two or more ECAPs responsive to two or more respective control pulses delivered during a time event may be recorded by sensing circuitry 212 during the same time event.

In some examples, therapy stimulation programs 217 may be updated according to a plurality of ECAPs received in response to the plurality of control pulses delivered to the patient according to ECAP test stimulation programs 218. For instance, processing circuitry 214 may update therapy stimulation programs 217 in real time by comparing one or more characteristics of ECAPs sensed by sensing circuitry 212 with target ECAP characteristics stored in memory 215 (e.g., patient ECAP characteristics 222). For example, processing circuitry 214 is configured to determine the amplitude of each ECAP signal received at sensing circuitry 212, and processing circuitry 214 is further configured to determine the representative amplitude of at least one respective ECAP signal and compare the representative amplitude of a series of ECAP signals to a target ECAP adjustment window (e.g., the target ECAP amplitude plus and minus a variance which is stored in patient ECAP characteristics 222). Target ECAP adjustment window may thus be a range of amplitudes deviating from target ECAP amplitude. For instance, the target ECAP adjustment window may span from a lower-bound amplitude value (e.g., the target ECAP amplitude minus the variance) to an upper-bound amplitude value (e.g., the target ECAP amplitude plus the variance). Generally, the lower-bound amplitude value is less than the target ECAP amplitude, and the upper-bound amplitude value is greater than target ECAP amplitude.

If the representative amplitude of the at least one respective ECAP signal (e.g., an amplitude of a single ECAP signal or an average of two or more ECAP amplitudes) is greater than the upper-bound amplitude value, processing circuitry 214 may adjust one or more of therapy stimulation programs 217 and ECAP test stimulation programs 218 to decrease the amplitude of informed pulses and control pulses following the at least one respective ECAP. The amplitude of informed pulses and control pulses may be decreased by different predetermined steps or different predetermined percentages. Additionally, if the representative amplitude of the at least one respective ECAP is less than the lower-bound amplitude value, processing circuitry 214 may adjust therapy stimulation programs 217 and ECAP test stimulation programs 218, and the programs 217 and 218 may instruct stimulation generator 211 to increase the amplitude of informed pulses and control pulses following the at least one respective ECAP. Moreover, if the representative amplitude of the at least one respective ECAP is greater than the lower-bound amplitude value and less than the upper-bound amplitude value, processing circuitry 214 may not change programs 217 and 218, and stimulation generator 211 may maintain the amplitude of the informed pulses following the at least one respective ECAP. In one example, adjusting the programs 217 and 218 may include changing one or more parameters of the plurality of informed pulses and the plurality of control pulses. In one example, the at least one respective ECAP may include a series of four consecutive ECAPs.

Processing circuitry 214, in one example, may change the amplitude of the informed pulses and the control pulses following the at least one respective ECAP inversely proportional to the difference between target ECAP amplitude and the representative amplitude of the at least one respective ECAP. For instance, if the representative amplitude of the at least one respective ECAP is 20% lower than target ECAP amplitude, then processing circuitry 214 may update therapy programs 217 and 218 such that the amplitude of informed pulses and the control pulses is increased by 20%. In one example, the representative amplitude may be the mean amplitude of two or more respective ECAP signals sensed by sensing circuitry 212. In other examples, the representative amplitude may be the median amplitude of two or more respective ECAP signal, or a rolling average of two or more respective ECAP signals.

In another example, processing circuitry 214 may determine the amplitude of a respective ECAP signal sensed by sensing circuitry 212. In response to a comparison between the amplitude of the respective ECAP signal and the target ECAP amplitude stored in patient ECAP characteristics 222, processing circuitry 214 may determine a percentage difference between the amplitude of the respective ECAP signal and target ECAP amplitude. Consequently, processing circuitry 214 may adjust the amplitude of subsequent informed pulses to be inversely proportional to the percentage difference between the amplitude of the respective ECAP and target ECAP amplitude.

In other examples, processing circuitry 214 may use the representative amplitude of the at least one respective ECAP to change other parameters of informed pulses to be delivered, such as pulse width, pulse frequency, and pulse shape. All of these parameters may contribute to the intensity of the informed pulses, and changing one or more of these parameter values may effectively adjust the informed pulse intensity to compensate for the changed distance between the stimulation electrodes and the nerves indicated by the representative amplitude of the ECAP signals.

In some examples, leads 230 may be linear 8-electrode leads (not pictured); sensing and stimulation delivery may each be performed using a different set of electrodes. In a linear 8-electrode lead, each electrode may be numbered consecutively from 0 through 7. For instance, a control pulse may be generated using electrode 1 as a cathode and electrodes 0 and 2 as anodes (e.g., a guarded cathode), and a respective ECAP signal may be sensed using electrodes 6 and 7, which are located on the opposite end of the electrode array. This strategy may minimize the interference of the stimulation pulse with the sensing of the respective ECAP. Other electrode combinations may be implemented, and the electrode combinations may be changed using the patient programmer via telemetry circuitry 213. For example, stimulation electrodes and sensing electrodes may be positioned closer together. Shorter pulse widths for the control pulses may allow the sensing electrodes to be closer to the stimulation electrodes.

ECAP feedback rules 221 may define how processing circuitry 214 uses the sensed ECAP signals as feedback for changing one or more parameters that define informed pulses and stored as therapy stimulation programs 217. For example, ECAP feedback rules 221 may specify that the percentage difference between the representative ECAP amplitude and the target ECAP amplitude is used to inversely adjust the current amplitude of informed pulses to the same proportion as the percentage difference, such as the technique described in FIG. 9. As another example, ECAP feedback rules 221 may specify that the difference between the target ECAP amplitude is multiplied by a gain value and added to the previous current amplitude of the informed pulses and control pulses as described in FIG. 11. In any case, ECAP feedback rules 221 may instruct processing circuitry 214 how to adjust informed pulses and/or control pulses based on the sensed ECAP signals.

In one example, sensor 216 may detect a change in activity or a change in posture of the patient. Processing circuitry 214 may receive an indication from sensor 216 that the activity level or posture of the patient is changed, and processing circuitry 214 may be configured to initiate or change the delivery of the plurality of control pulses according to the ECAP test stimulation programs 218. For example, processing circuitry 214 may increase the frequency of control pulse delivery and respective ECAP sensing in response to receiving an indication that the patient activity has increased, which may indicate that the distance between electrodes and nerves will likely change. Alternatively, processing circuitry 214 may decrease the frequency of control pulse delivery and respective ECAP sensing in response to receiving an indication that the patient activity has decreased. In some examples, one or more parameters (e.g., frequency, amplitude, slew rate, pulse duration, or the like) may be adjusted (e.g., increased or decreased) in response to receiving an indication that the patient activity has changed. Processing circuitry 214 may be further configured to update therapy stimulation programs 217 and ECAP test stimulation programs 218 according to the signal received from sensor 216.

Figure 2B:
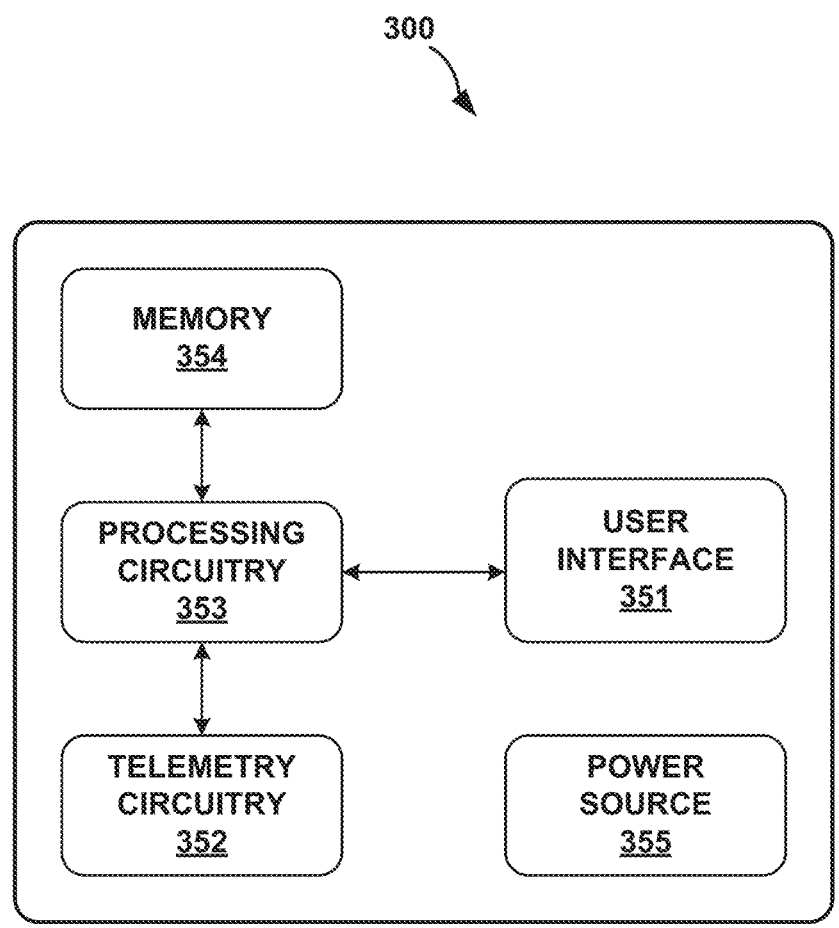
FIG. 2B is a block diagram of the example external programmer of FIG. 1.

FIG. 2B is a block diagram of the example external programmer 300. External programmer 300 may be an example of external programmer 150 of FIG. 1. Although programmer 300 may generally be described as a hand-held device, programmer 300 may be a larger portable device or a more stationary device. In addition, in other examples, programmer 300 may be included as part of an external charging device or include the functionality of an external charging device. As illustrated in FIG. 2B, programmer 300 may include a processing circuitry 353, memory 354, user interface 351, telemetry circuitry 352, and power source 355. Memory 354 may store instructions that, when executed by processing circuitry 353, cause processing circuitry 353 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 353 may include processing circuitry configured to perform the processes discussed with respect to processing circuitry 353.

In general, programmer 300 comprises any suitable arrangement of hardware, alone or in combination with software and/or firmware, to perform the techniques attributed to programmer 300, and processing circuitry 353, user interface 351, and telemetry circuitry 352 of programmer 300. In various examples, programmer 300 may include one or more processors, such as one or more microprocessors, DSPs, ASICs, FPGAs, or any other equivalent integrated or discrete logic circuitry, as well as any combinations of such components. Programmer 300 also, in various examples, may include a memory 354, such as RAM, ROM, PROM, EPROM, EEPROM, flash memory, a hard disk, a CD-ROM, comprising executable instructions for causing the one or more processors to perform the actions attributed to them. Moreover, although processing circuitry 353 and telemetry circuitry 352 are described as separate modules, in some examples, processing circuitry 353 and telemetry circuitry 352 are functionally integrated. In some examples, processing circuitry 353 and telemetry circuitry 352 correspond to individual hardware units, such as ASICs, DSPs, FPGAs, or other hardware units.

Memory 354 (e.g., a storage device) may store instructions that, when executed by processing circuitry 353, cause processing circuitry 353 and programmer 300 to provide the functionality ascribed to programmer 300 throughout this disclosure. For example, memory 354 may include instructions that cause processing circuitry 353 to obtain a parameter set from memory, select a spatial electrode movement pattern, or receive a user input and send a corresponding command to IMD 300, or instructions for any other functionality. In addition, memory 354 may include a plurality of programs, where each program includes a parameter set that defines therapy stimulation or control stimulation. Memory 354 may also store data received from a medical device (e.g., IMD 110). For example, memory 354 may store ECAP related data recorded at a sensing module of the medical device, and memory 354 may also store data from one or more sensors of the medical device.

User interface 351 may include a button or keypad, lights, a speaker for voice commands, a display, such as a liquid crystal (LCD), light-emitting diode (LED), or organic light-emitting diode (OLED). In some examples the display may be a touch screen. User interface 351 may be configured to display any information related to the delivery of electrical stimulation, identified patient behaviors, sensed patient parameter values, patient behavior criteria, or any other such information. User interface 351 may also receive user input via user interface 351. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Telemetry circuitry 352 may support wireless communication between the medical device and programmer 300 under the control of processing circuitry 353. Telemetry circuitry 352 may also be configured to communicate with another computing device via wireless communication techniques, or direct communication through a wired connection. In some examples, telemetry circuitry 352 provides wireless communication via an RF or proximal inductive medium. In some examples, telemetry circuitry 352 includes an antenna, which may take on a variety of forms, such as an internal or external antenna.

Examples of local wireless communication techniques that may be employed to facilitate communication between programmer 300 and IMD 110 include RF communication according to the 802.11 or Bluetooth specification sets or other standard or proprietary telemetry protocols. In this manner, other external devices may be capable of communicating with programmer 300 without needing to establish a secure wireless connection. As described herein, telemetry circuitry 352 may be configured to transmit a spatial electrode movement pattern or other stimulation parameter values to IMD 110 for delivery of electrical stimulation therapy.

In some examples, selection of parameters or therapy stimulation programs may be transmitted to the medical device for delivery to the patient. In other examples, the therapy may include medication, activities, or other instructions that the patient must perform themselves or a caregiver perform for the patient. In some examples, programmer 300 may provide visual, audible, and/or tactile notifications that indicate there are new instructions. Programmer 300 may require receiving user input acknowledging that the instructions have been completed in some examples.

According to the techniques of the disclosure, user interface 351 of external programmer 300 receives an indication from a clinician instructing a processor of the medical device to update one or more therapy stimulation programs or to update one or more ECAP test stimulation programs. Updating therapy stimulation programs and ECAP test stimulation programs may include changing one or more parameters of the stimulation pulses delivered by the medical device according to the programs, such as amplitude, pulse width, frequency, and pulse shape of the informed pulses and/or control pulses. User interface 351 may also receive instructions from the clinician commanding any electrical stimulation, including therapy stimulation and control stimulation to commence or to cease.

The architecture of programmer 300 illustrated in FIG. 2B is shown as an example. The techniques as set forth in this disclosure may be implemented in the example programmer 300 of FIG. 2B, as well as other types of systems not described specifically herein. Nothing in this disclosure should be construed so as to limit the techniques of this disclosure to the example architecture illustrated by FIG. 2B.

Figure 3:
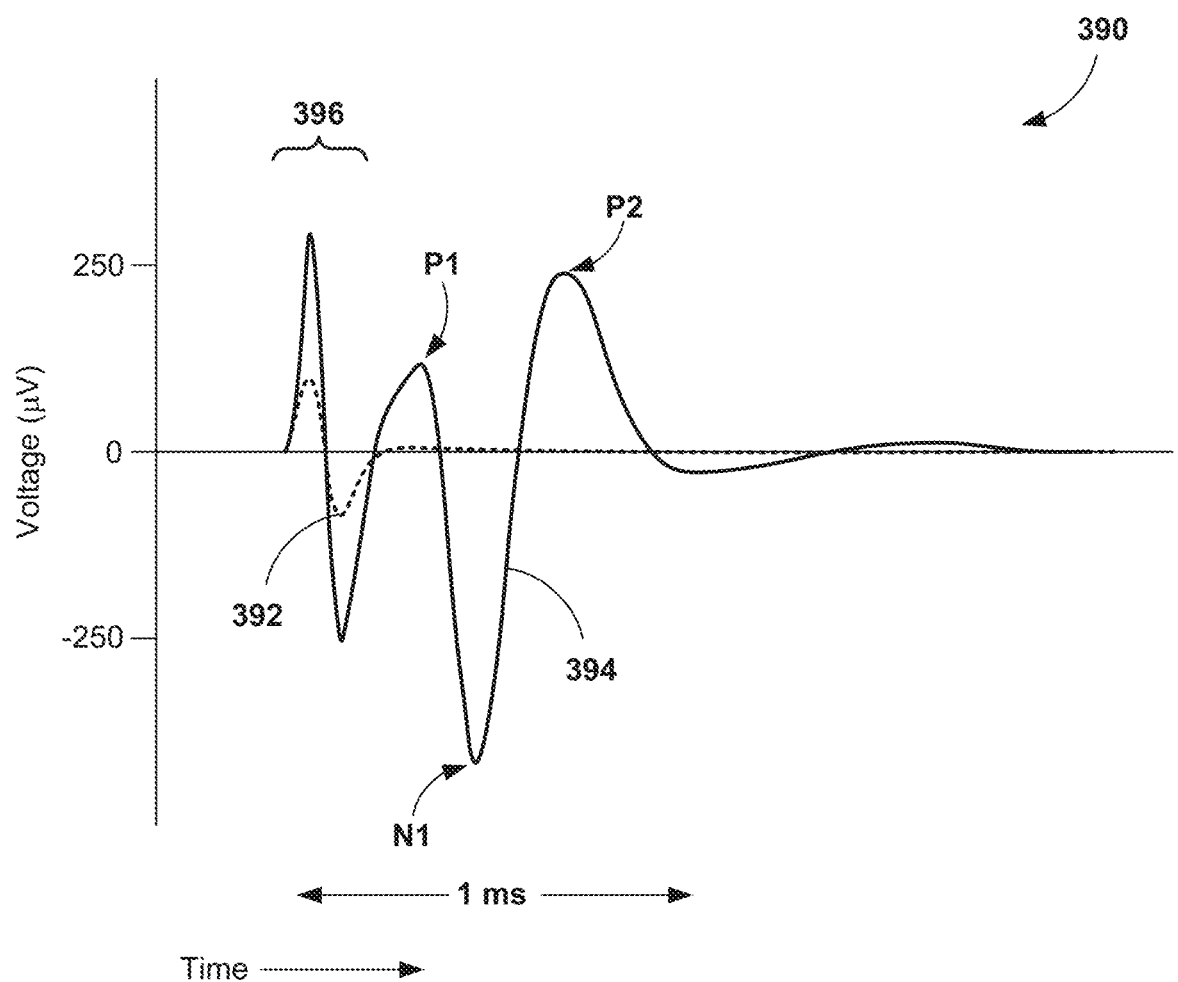
FIG. 3 is a graph of an example evoked compound action potentials (ECAPs) sensed for respective stimulation pulses.

FIG. 3 is a graph 390 of an example evoked compound action potentials (ECAPs) sensed for respective stimulation pulses. As shown in FIG. 3, graph 390 shows example ECAP signal 392 (dotted line) and ECAP signal 394 (solid line). Each of ECAP signals 392 and 394 may be sensed from control pulses that were delivered from a guarded cathode and bi-phasic pulses including an interphase interval between each positive and negative phase of the pulse. The guarded cathode of the stimulation electrodes may be located at the end of an 8-electrode lead while two sensing electrodes are provided at the other end of the 8-electrode lead. ECAP signal 392 illustrates the voltage amplitude sensed as a result from a sub-threshold stimulation pulse. Peaks 396 of ECAP signal 392 are detected and represent the artifact of the delivered control pulse. However, no propagating signal is detected after the artifact in ECAP signal 392 because the control pulse was sub-threshold.

In contrast to ECAP signal 392, ECAP signal 394 represents the voltage amplitude detected from a supra-threshold control pulse. Peaks 396 of ECAP signal 394 are detected and represent the artifact of the delivered control pulse. After peaks 396, ECAP signal 394 also includes peaks P1, N1, and P2, which are three typical peaks representative of propagating action potentials from an ECAP. The example duration of the artifact and peaks P1, N1, and P2 is approximately 1 millisecond (ms). When detecting the ECAP of ECAP signal 394, different characteristics may be identified. For example, the characteristic of the ECAP may be the amplitude between N1 and P2. This N1-P2 amplitude may be easily detectable even if the artifact impinges on P1, a relatively large signal, and the N1-P2 amplitude may be minimally affected by electronic drift in the signal. In other examples, the characteristic of the ECAP used to control informed pulses may be an amplitude of P1, N1, or P2 with respect to neutral or zero voltage. In some examples, the characteristic of the ECAP used to control informed pulses may be a sum of two or more of peaks P1, N1, or P2. In other examples, the characteristic of ECAP signal 394 may be the area under one or more of peaks P1, N1, and/or P2. In other examples, the characteristic of the ECAP may be a ratio of one of peaks P1, N1, or P2 to another one of the peaks. In some examples, the characteristic of the ECAP may be a slope between two points in the ECAP signal, such as the slope between N1 and P2. In other examples, the characteristic of the ECAP may be the time between two points of the ECAP, such as the time between N1 and P2. The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal increases with increased amplitude of the control pulse, as long as the pulse amplitude is greater than threshold such that nerves depolarize and propagate the signal. The target ECAP characteristic (e.g., the target ECAP amplitude) may be determined from the ECAP signal detected from a control pulse when informed pulses are determined to deliver effective therapy to the patient. The ECAP signal thus is representative of the distance between the stimulation electrodes and the nerves appropriate for the stimulation parameter values of the informed pulses delivered at that time. Therefore, IMD 110 may attempt to use detected changes to the measured ECAP characteristic value to change informed pulse parameter values and maintain the target ECAP characteristic value during informed pulse delivery.

Figure 4A:
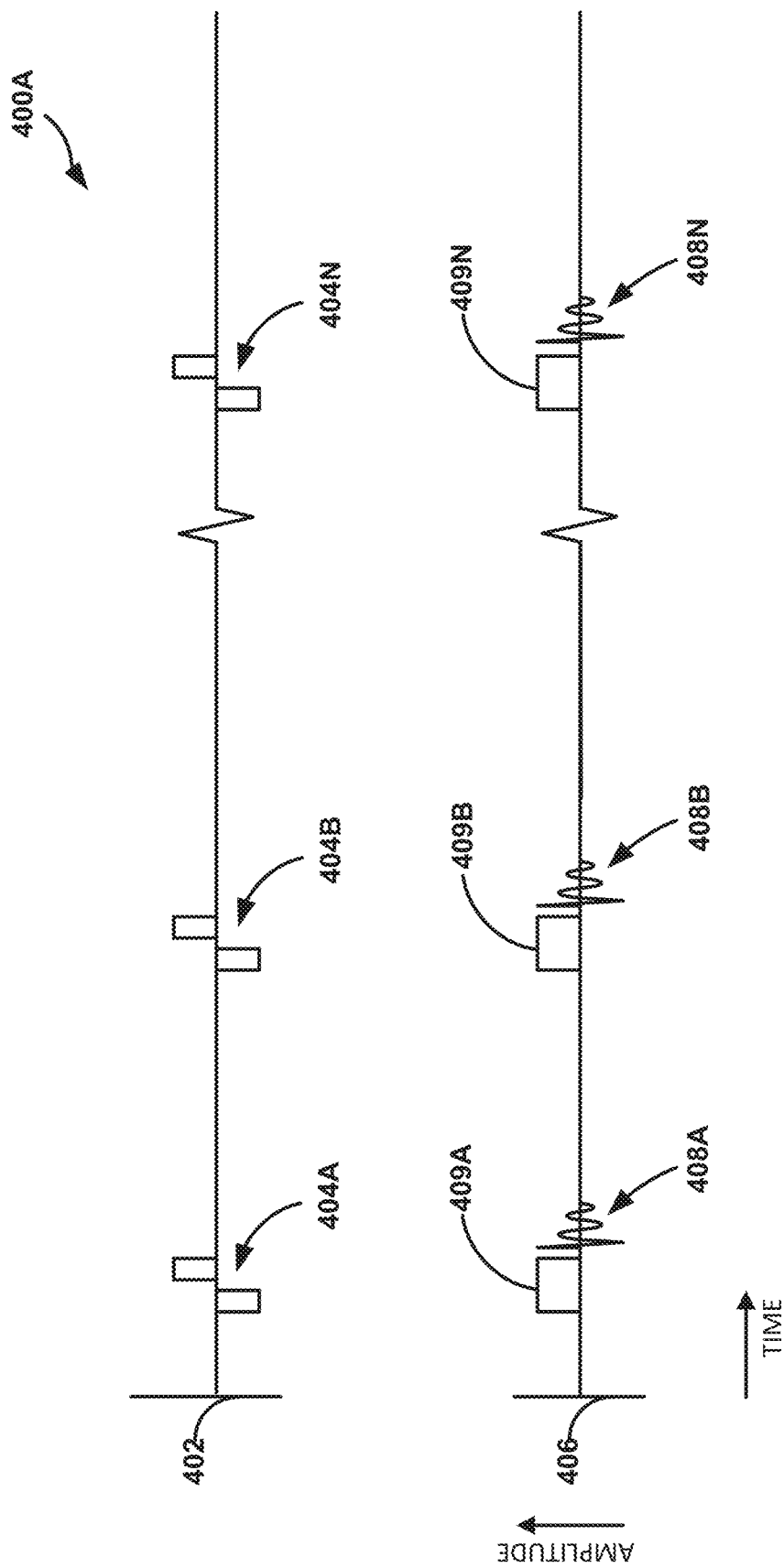
FIG. 4A is a timing diagram illustrating an example of electrical stimulation pulses and respective sensed ECAPs, in accordance with one or more techniques of this disclosure.

FIG. 4A is a timing diagram 400A illustrating an example of electrical stimulation pulses and respective sensed ECAP signals, in accordance with one or more techniques of this disclosure. For example, FIG. 4A is described with reference to IMD 200 of FIG. 2. As illustrated, timing diagram 400A includes first channel 402, a plurality of control pulses 404A-404N (collectively "control pulses 404"), second channel 406, a plurality of respective ECAPs 408A-408N (collectively "ECAPs 408"), and a plurality of stimulation interference signals 409A-409N (collectively "stimulation interference signals 409"). In the example of FIG. 4A, control pulses 404 may also provide therapy to the patient and informed pulses are not necessary for therapy.

First channel 402 is a time/voltage (and/or current) graph indicating the voltage (or current) of at least one electrode of electrodes 232, 234. In one example, the stimulation electrodes of first channel 402 may be located on the opposite side of the lead as the sensing electrodes of second channel 406. Control pulses 404 may be electrical pulses delivered to the spinal cord of the patient by at least one of electrodes 232, 234, and control pulses 404 may be balanced biphasic square pulses with an interphase interval. In other words, each of control pulses 404 are shown with a negative phase and a positive phase separated by an interphase interval. For example, a control pulse 404 may have a negative voltage for the same amount of time and amplitude that it has a positive voltage. It is noted that the negative voltage phase may be before or after the positive voltage phase. Control pulses 404 may be delivered according to ECAP test stimulation programs 218 stored in memory 215 of IMD 200, and ECAP test stimulation programs 218 may be updated according to user input via an external programmer and/or may be updated according to a signal from sensor 216. In one example, control pulses 404 may have a pulse width of less than approximately 300 microseconds (e.g., the total time of the positive phase, the negative phase, and the interphase interval is less than 300 microseconds). In another example, control pulses 404 may have a pulse width of approximately 100 µs for each phase of the bi-phasic pulse. As illustrated in FIG. 4A, control pulses 404 may be delivered via one or more electrodes that deliver or sense signals corresponding to channel 402. Delivery of control pulses 404 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode. For some patients, control pulses 404 may sufficiently provide therapy that treats the condition and/or symptoms of the patient. Therefore, additional informed pulses may not be needed for these patients or for at least some aspect of the therapy for these patients.

Second channel 406 is a time/voltage (and/or current) graph indicating the voltage (or current) of at least one electrode of electrodes 232, 234. In one example, the electrodes of second channel 406 may be located on the opposite side of the lead as the electrodes of first channel 402. ECAPs 408 may be sensed at electrodes 232, 234 from the spinal cord of the patient in response to control pulses 404. ECAPs 408 are electrical signals which may propagate along a nerve away from the origination of control pulses 404. In one example, ECAPs 408 are sensed by different electrodes than the electrodes used to deliver control pulses 404. As illustrated in FIG. 4A, ECAPs 408 may be recorded on second channel 406.

Stimulation interference signals 409A, 409B, and 409N (e.g., the artifact of the stimulation pulses) may be sensed by leads 230 and may be sensed during the same period of time as the delivery of control pulses 404. Since the interference signals may have a greater amplitude and intensity than ECAPs 408, any ECAPs arriving at IMD 200 during the occurrence of stimulation interference signals 409 may not be adequately sensed by sensing circuitry 206 of IMD 200. However, ECAPs 408 may be sufficiently sensed by sensing circuitry 206 because each ECAP 408 falls after the completion of each a control pulse 404. As illustrated in FIG. 4A, stimulation interference signals 409 and ECAPs 408 may be recorded on channel 406.

FIG. 4B is a timing diagram 400B illustrating one example of electrical stimulation pulses and respective sensed ECAPs according to some techniques of the disclosure. For convenience, FIG. 4B is described with reference to IMD 200 of FIG. 2A. As illustrated, timing diagram 400B includes first channel 410, a plurality of control pulses 412A-412N (collectively "control pulses 412"), second channel 420, a plurality of informed pulses 424A-424N (collectively "informed pulses 424") including passive recharge phases 426A-426N (collectively passive recharge phases 426"), third channel 430, a plurality of respective ECAPs 436A-436N (collectively "ECAPs 436"), and a plurality of stimulation interference signals 438A-438N (collectively "stimulation interference signals 438").

First channel 410 is a time/voltage (and/or current) graph indicating the voltage (or current) of at least one electrode of electrodes 232, 234. In one example, the stimulation electrodes of first channel 410 may be located on the opposite side of the lead as the sensing electrodes of third channel 430. Control pulses 412 may be electrical pulses delivered to the spinal cord of the patient by at least one of electrodes 232, 234, and control pulses 412 may be balanced biphasic square pulses with an interphase interval. In other words, each of control pulses 412 are shown with a negative phase and a positive phase separated by an interphase interval. For example, a control pulse 412 may have a negative voltage for the same amount of time and amplitude that it has a positive voltage. It is noted that the negative voltage phase may be before or after the positive voltage phase. Control pulses 412 may be delivered according to ECAP test stimulation programs 218 stored in memory 250 of IMD 200, and ECAP test stimulation programs 218 may be updated according to user input via an external programmer and/or may be updated according to a signal from sensor 216. In one example, control pulses 412 may have a pulse width of less than approximately 300 microseconds (e.g., the total time of the positive phase, the negative phase, and the interphase interval is less than 300 microseconds). In another example, control pulses 412 may have a pulse width of approximately 100 µs for each phase of the bi-phasic pulse. As illustrated in FIG. 4B, control pulses 412 may be delivered via one or more electrodes that deliver or sense signals corresponding to channel 410. Delivery of control pulses 412 may be delivered by leads 230 in a guarded cathode electrode combination. For example, if leads 230 are linear 8-electrode leads, a guarded cathode combination is a central cathodic electrode with anodic electrodes immediately adjacent to the cathodic electrode.

Second channel 420 is a time/voltage (and/or current) graph indicating the voltage (or current) of at least one electrode of electrodes 232, 234 for the informed pulses. In one example, the electrodes of second channel 420 may partially or fully share common electrodes with the electrodes of first channel 410 and third channel 430. Informed pulses 424 may also be delivered by the same leads 230 that are configured to deliver control pulses 412. Informed pulses 424 may be interleaved with control pulses 412, such that the two types of pulses are not delivered during overlapping periods of time. However, informed pulses 424 may or may not be delivered by exactly the same electrodes that deliver control pulses 412. Informed pulses 424 may be monophasic pulses with pulse widths of greater than approximately 300 µs and less than approximately 1000 µs. In fact, informed pulses 424 may be configured to have longer pulse widths than control pulses 412. As illustrated in FIG. 4B, informed pulses 424 may be delivered on channel 420.

Informed pulses 424 may be configured for passive recharge. For example, each informed pulse 424 may be followed by a passive recharge phase 426 to equalize charge on the stimulation electrodes. Unlike a pulse configured for active recharge, wherein remaining charge on the tissue following a stimulation pulse is instantly removed from the tissue by an opposite applied charge, passive recharge allows tissue to naturally discharge to some reference voltage (e.g., ground or a rail voltage) following the termination of the informed pulse. In some examples, the electrodes of the medical device may be grounded at the medical device body. In this case, following the termination of informed pulse 424, the charge on the tissue surrounding the electrodes may dissipate to the medical device, creating a rapid decay of the remaining charge at the tissue following the termination of the pulse. This rapid decay is illustrated in passive recharge phases 426. Passive recharge phase 426 may have a duration in addition to the pulse width of the preceding informed pulse 424. In other examples (not pictured in FIG. 4B), informed pulses 424 may be bi-phasic pulses having a positive and negative phase (and, in some examples, an interphase interval between each phase) which may be referred to as pulses including active recharge. A informed pulse that is a bi-phasic pulse may or may not have a following passive recharge phase. Informed pulses 424 may be defined, and be a part of one or more stimulation programs. Although each of informed pulses 424 are illustrated as having the same parameter values (e.g., the same pulse width, amplitude, and pulse shape), some of informed pulses 424 may have one or more parameters that have different values from each other.

Third channel 430 is a time/voltage (and/or current) graph indicating the voltage (or current) of at least one electrode of electrodes 232, 234. In one example, the electrodes of third channel 430 may be located on the opposite side of the lead as the electrodes of first channel 410. ECAPs 436 may be sensed at electrodes 232, 234 from the spinal cord of the patient in response to control pulses 412. ECAPs 436 are electrical signals which may propagate along a nerve away from the origination of control pulses 412. In one example, ECAPs 436 are sensed by different electrodes than the electrodes used to deliver control pulses 412. As illustrated in FIG. 4B, ECAPs 436 may be recorded on third channel 430.

Stimulation interference signals 438A, 438B, and 438N (e.g., the artifact of the stimulation pulses) may be sensed by leads 230 and may be sensed during the same period of time as the delivery of control pulses 412 and informed pulses 424. Since the interference signals may have a greater amplitude and intensity than ECAPs 436, any ECAPs arriving at IMD 200 during the occurrence of stimulation interference signals 438 may not be adequately sensed by sensing circuitry 212 of IMD 200. However, ECAPs 436 may be sufficiently sensed by sensing circuitry 212 because each ECAP 436 falls after the completion of each a control pulse 412 and before the delivery of the next informed pulse 424. As illustrated in FIG. 4B, stimulation interference signals 438 and ECAPs 436 may be recorded on channel 430.

Figure 5:
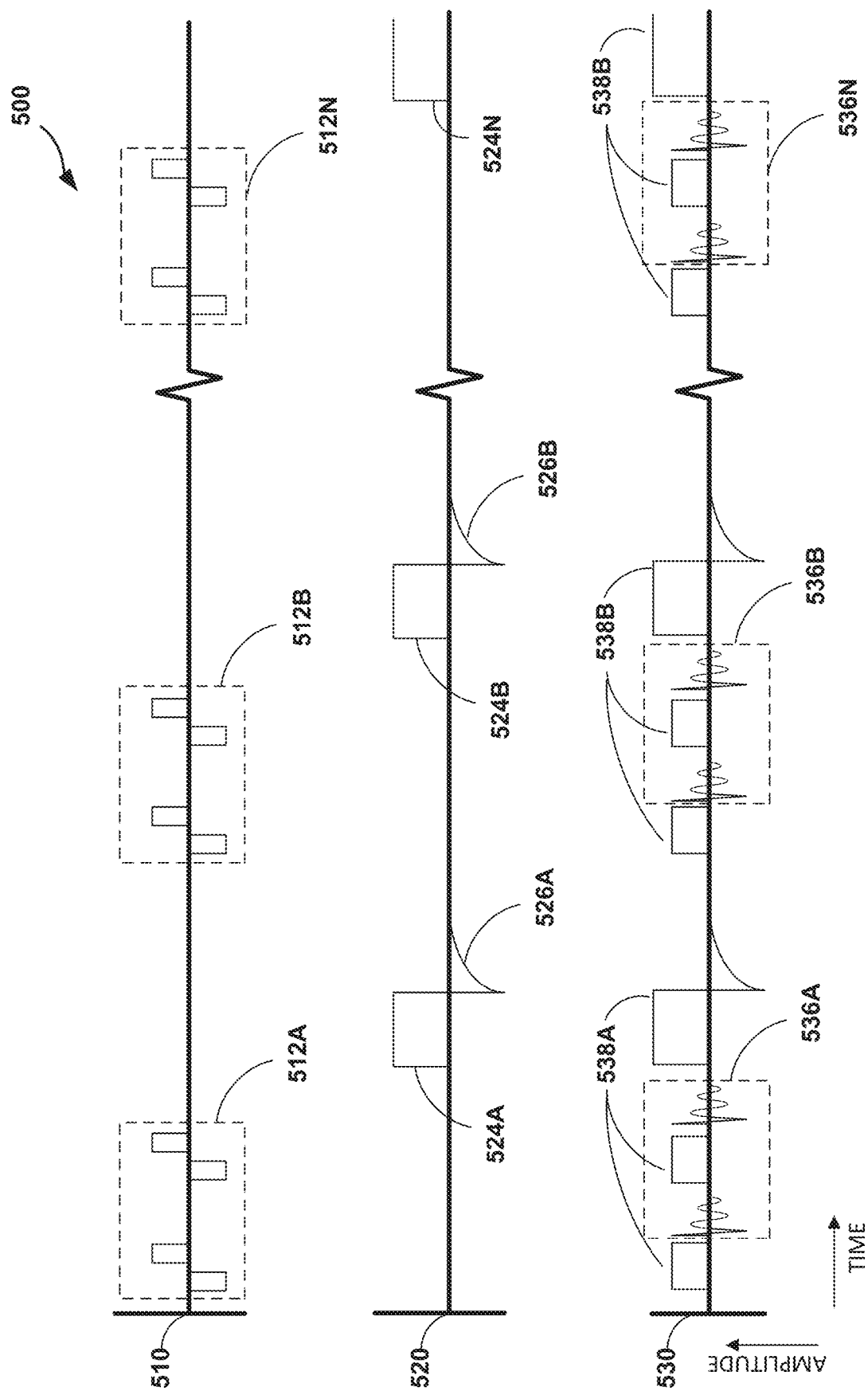
FIG. 5 is a timing diagram illustrating another example of electrical stimulation pulses and respective ECAPs according to the techniques of the disclosure.

FIG. 5 is a timing diagram 500 illustrating another example of electrical stimulation pulses and respective ECAPs according to the techniques of the disclosure. For convenience, FIG. 5 is described with reference to IMD 200 of FIG. 2A. As illustrated, timing diagram 500 includes first channel 510, a plurality of control pulses 512A-512N (collectively "control pulses 512"), second channel 520, a plurality of informed pulses 524A-524N (collectively "informed pulses 524") including passive recharge phases 526A-526N (collectively "passive recharge phases 526"), third channel 530, a plurality of respective ECAPs 536A-536N (collectively "ECAPs 536"), and a plurality of stimulation interference signals 538A-538N (collectively "stimulation interference signals 538"). FIG. 5 may be substantially similar to FIG. 4B, except for the differences detailed below.

Two or more (e.g. two) control pulses 512 may be delivered during each time event (e.g., window) of a plurality of time events, and each time event represents a time between two consecutive informed pulses 524. For example, during each time event, a first control pulse may be directly followed by a first respective ECAP, and subsequent to the completion of the first respective ECAP, a second control pulse may be directly followed by a second respective ECAP. Informed pulses may commence following the second respective ECAP. In other examples not illustrated here, three or more control pulses 512 may be delivered, and respective ECAP signals sensed, during each time event of the plurality of time events.

Figure 6:
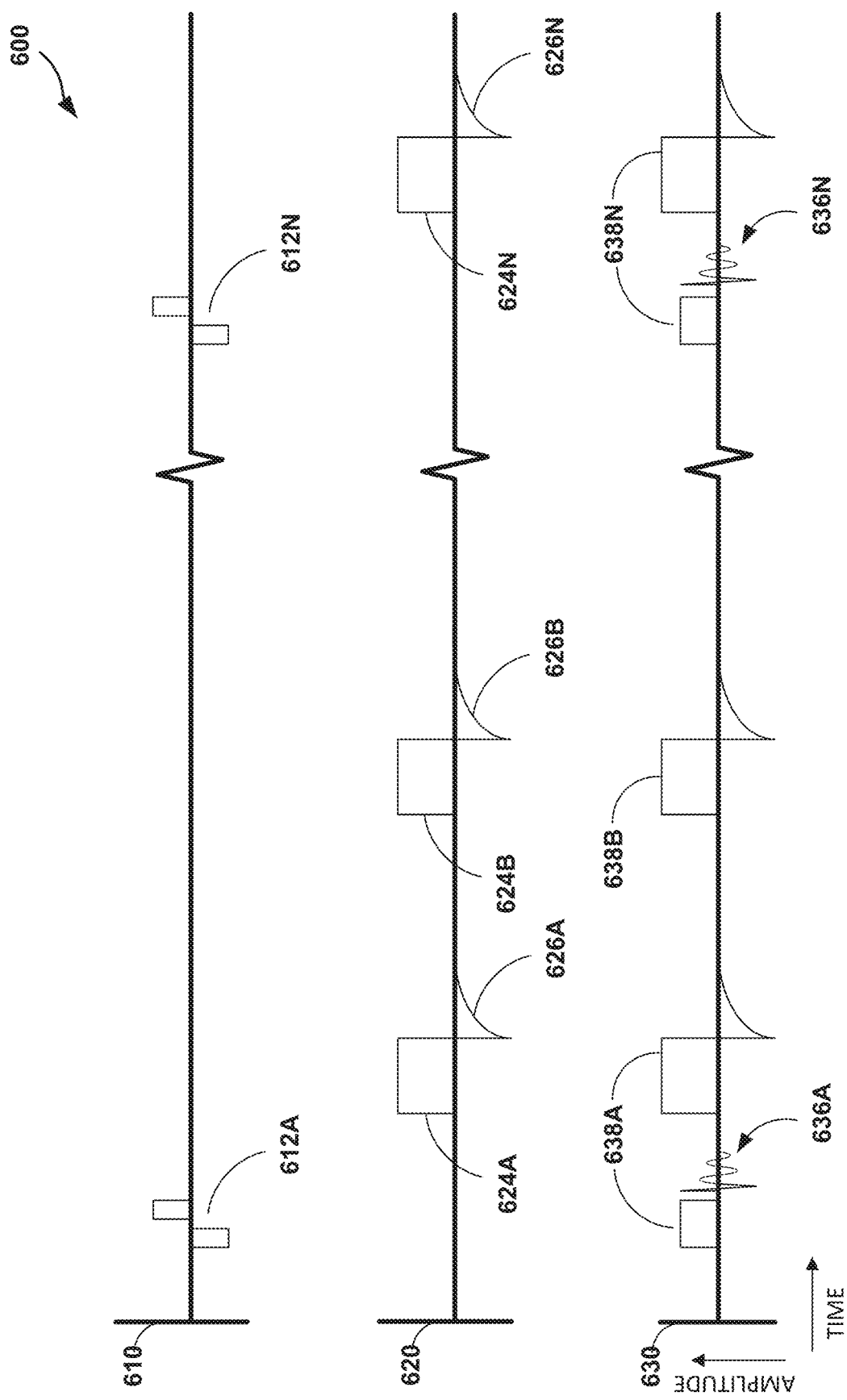
FIG. 6 is a timing diagram illustrating another example of electrical stimulation pulses and respective ECAPs according to the techniques of the disclosure.

FIG. 6 is a timing diagram 600 illustrating another example of electrical stimulation pulses and respective ECAPs according to the techniques of the disclosure. For convenience, FIG. 6 is described with reference to IMD 200 of FIG. 2A. As illustrated, timing diagram 600 includes first channel 610, a plurality of control pulses 612A-612N (collectively "control pulses 612"), second channel 620, a plurality of informed pulses 624A-624N (collectively "informed pulses 624") including passive recharge phases 626A-626N (collectively "passive recharge phases 626"), third channel 630, a plurality of respective ECAPs 636A-636N (collectively "ECAPs 636"), and a plurality of stimulation interference signals 438A-438N (collectively "stimulation interference signals 438"). FIG. 6 may be substantially similar to FIG. 4B, except for the differences detailed below.

In previous examples illustrated in FIG. 4B and FIG. 5, at least one control pulse was delivered and interleaved between each pair of consecutive informed pulses. However, in some examples, control pulses 612 are not delivered during each time event (or window) of the plurality of time events, wherein each time event represents a time between two consecutive informed pulses 624. As illustrated in the example of FIG. 6, a control pulse 612 is not delivered following informed pulse 624A and preceding informed pulse 624B. In other words, consecutive informed pulses 624A and 624B may be delivered without an intervening control pulse. In any case, informed pulses are delivered according to a predetermined frequency, and control pulses may be delivered at any time between the informed pulses. In some examples, the parameter values of both informed pulse 624A and informed pulse 624B may be the same because they are defined by the same stimulation program. In other examples, informed pulse 624A and informed pulse 624B may have at least one stimulation parameter that differs in value, such as a different amplitude, pulse width, pulse frequency, or electrode combination. In this manner, informed pulse 624A may be a part of a first stimulation program while informed pulse 624B may be part of a second stimulation program that is different than the first stimulation program. Processing circuitry 214 may thus delivery informed pulses from two or more different stimulation programs, where processing circuitry 214 uses the detected ECAP signal from the same control pulse (e.g., control pulse 612A) to "inform" or otherwise adjust one or more parameter values of the informed pulses in multiple stimulation programs (e.g., both of informed pulses 624A and 624B). This concept of multiple stimulation programs may be applied to any informed pulses described herein.

Control pulses may be administered according to ECAP test stimulation programs 218. Processing circuitry 214 may be configured to update ECAP test stimulation programs according to user input via telemetry circuitry 213, and also by a signal from sensor 216. For example, a clinician may operate a patient programmer and send a signal to telemetry circuitry 213 including instructions for updating ECAP test stimulation programs 218. The clinician may set control stimulation to any of the examples illustrated in FIGS. 4-6, and the clinician also may customize control stimulation to a configuration not illustrated in FIGS. 4-6. The clinician may elect to cease control stimulation or commence control stimulation at any time. In some examples, a detection that the patient's posture or activity level has changed will initiate control stimulation.

Figure 7:
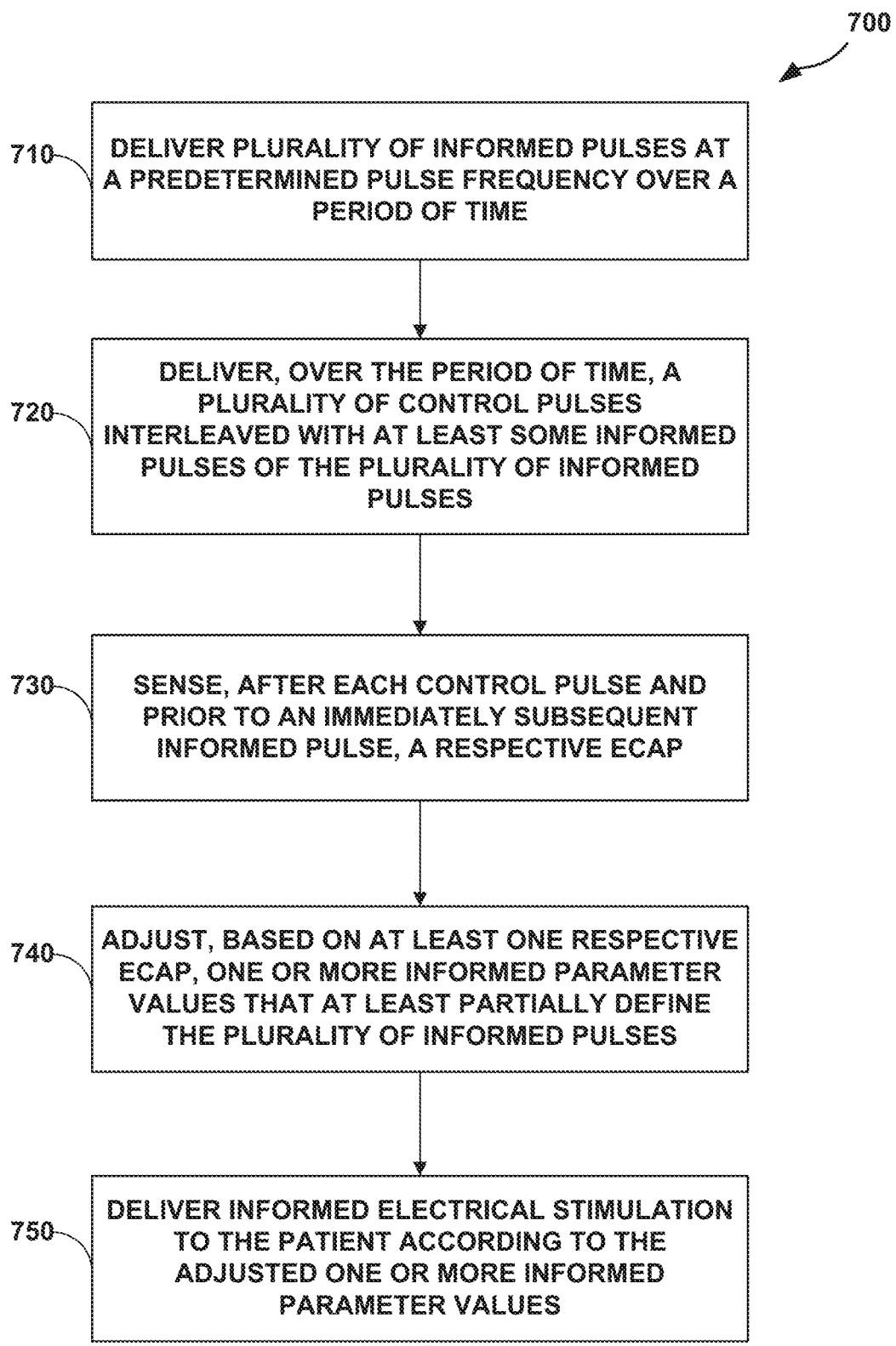
FIG. 7 is a flowchart illustrating an example technique for therapy delivery according to the techniques of this disclosure.

FIG. 7 is a flowchart illustrating an example operation 700 for therapy delivery according to the techniques of this disclosure. For convenience, FIG. 7 is described with respect to IMD 110 of FIG. 1. However, the techniques of FIG. 7 may be performed by different components of IMD 110 or by additional or alternative medical devices.

In the example of FIG. 7, IMD 110 may deliver electrical stimulation therapy to patient 105, the electrical stimulation therapy comprising a plurality of informed pulses at a predetermined pulse frequency over a period of time (710). Furthermore, IMD 110 may deliver, over the period of time, a plurality of control pulses interleaved with at least some informed pulses of the plurality of informed pulses (720). As described herein, the control pulses may or may not be configured to contribute to therapy for the patient. For example, one or more control pulses may be delivered between consecutive informed pulses. As another example, one or more informed pulses may be delivered between consecutive control pulses. IMD 110 may sense, after one or more control pulses of the plurality of control pulses and prior to an immediately subsequent informed pulse of the plurality of informed pulses, a respective ECAP (730). Subsequent to the sensing, IMD 110 may adjust, based on at least one respective ECAP, one or more parameter values that at least partially define the plurality of informed pulses of the electrical stimulation therapy (740). For example, IMD 110 may compare a value of a characteristic of the sensed ECAP to a target ECAP characteristic value and adjust the informed pulses and, in some examples, the control pulses to maintain the target ECAP characteristic vale. IMD 110 may deliver, via leads 130, the electrical stimulation therapy to spinal cord 120 of patient 105 according to the adjusted one or more parameter values (750).

Figure 8:
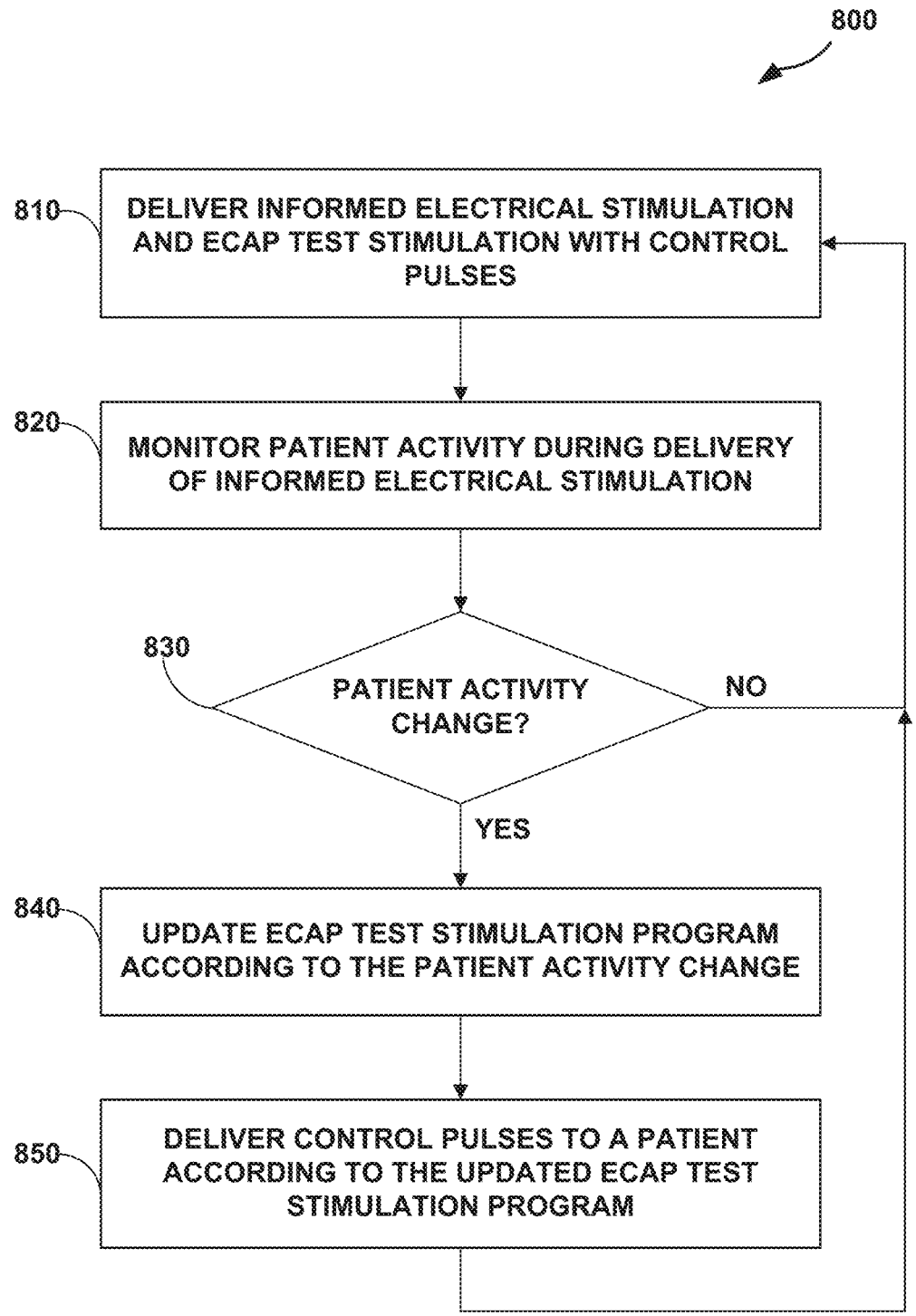
FIG. 8 is a flowchart illustrating an example technique for adjusting the delivery of control pulses of ECAP test stimulation in response to an input.

FIG. 8 is a flowchart illustrating an example operation 800 for delivery of control pulses in response to sensor input. For convenience, FIG. 8 is described with respect to IMD 200 of FIG. 2A. However, the techniques of FIG. 8 may be performed by different components of IMD 200 or by additional or alternative medical devices.

In the example of FIG. 8, processing circuitry 214 may deliver electrical stimulation therapy (e.g., informed pulses) and ECAP test stimulation with control pulses (810). Processing circuitry 214 monitors patient activity during the delivery of the electrical stimulation therapy (820). The patient activity may include changes in patient movement, switching to different postures, or any other type of activity which may cause the electrodes to move with respect to the target tissue (e.g., neurons).

If processing circuitry 214 does not detect any patient activity change ("NO" branch of block 830), processing circuitry 214 may then continue to deliver electrical stimulation therapy (810). If processing circuitry 214 does detect a patient activity change ("YES" branch of block 830), processing circuitry 214 may update the ECAP test stimulation program according to the patient activity change (840). For example, processing circuitry 214 may increase the frequency that control pulses are delivered and ECAP signals are sensed in response to detecting an increase in patient activity. In some examples, this increase in frequency may continue for a specified period of time or indefinitely. Processing circuitry 214 may then control the stimulation generator 211 to deliver the control pulses to the patient according to the updated. ECAP test stimulation program (850) and continue delivering electrical stimulation therapy (810). In other examples, processing circuitry 214 may update an ECAP test stimulation program in response to receiving a user input indicating that an activity has changed or will be changing soon. Alternatively, a patient may request increased frequency of ECAP sensing if the patient believes that stimulation therapy is not adjusting to activity or posture changes in an adequate amount of time.

Figure 9:
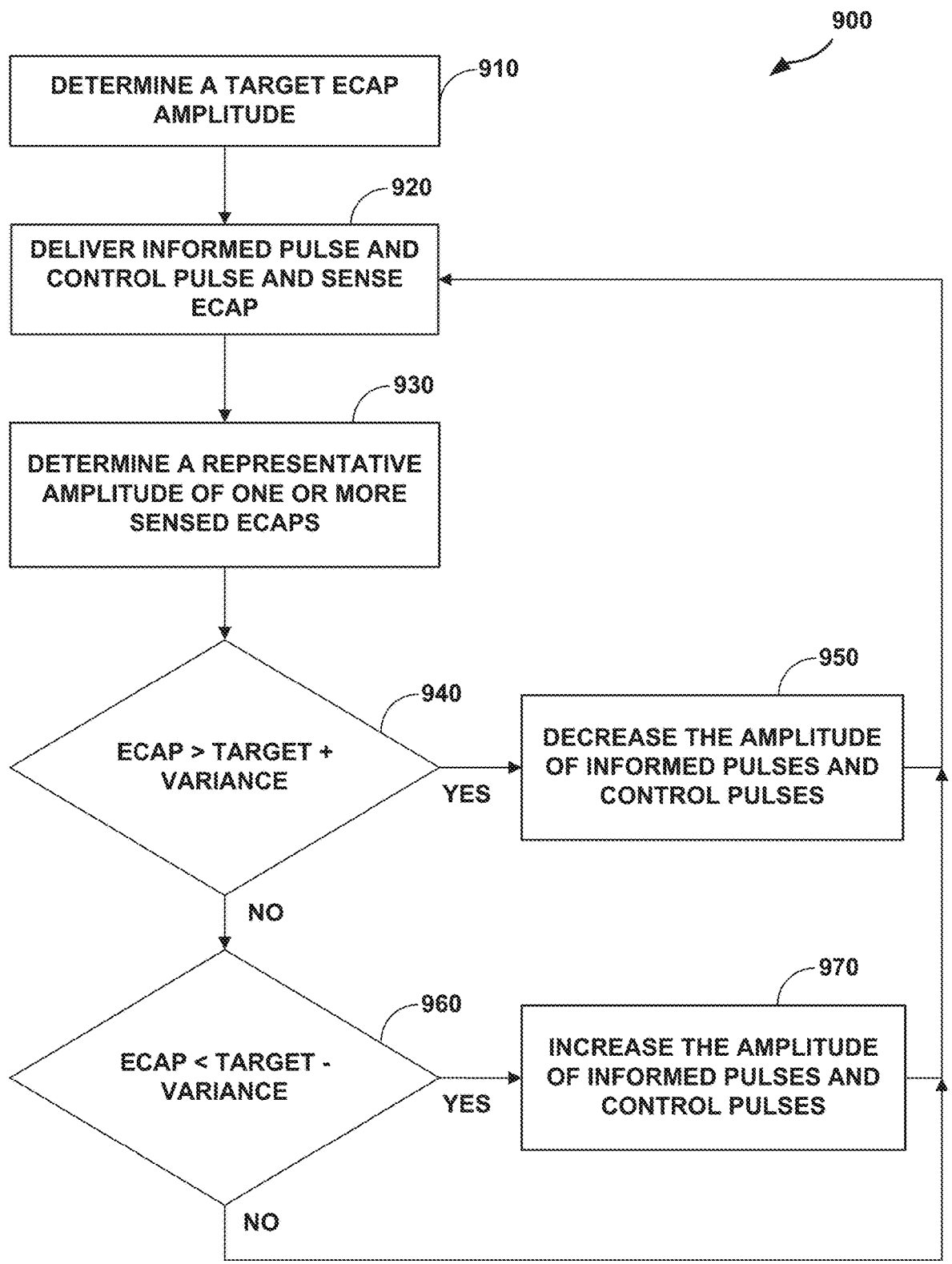
FIG. 9 is a flowchart illustrating an example technique for adjusting stimulation therapy.

FIG. 9 is a flowchart illustrating an example operation 900 for therapy delivery according to the techniques of this disclosure. For convenience, FIG. 9 is described with respect to IMD 200 of FIG. 2A. However, the techniques of FIG. 9 may be performed by different components of IMD 200 or by additional or alternative medical devices. Operation 900 is an example feedback mechanism for controlling stimulation therapy using sensed ECAP signals.

As illustrated in FIG. 9, processing circuitry 214 of IMD 200 may determine a target ECAP amplitude (910). The target ECAP amplitude may be indicated in patient ECAP characteristics 222 stored in IMD 200. One example target ECAP amplitude may be the N1-P2 amplitude detectable in the ECAP signal. In other examples, processing circuitry 214 may automatically change the target ECAP amplitude over a period of time according to a predetermined function (e.g., a sinusoid function, step function, exponential function, or other schedule). Processing circuitry 214 then delivers an informed pulse and a control pulse and senses the resulting ECAP elicited by the control pulse (920). Processing circuitry 214 then determines a representative amplitude of one or more sensed ECAPs (930). For example, the representative amplitude may be the average amplitude of the last four sensed ECAP signals. However, the representative amplitude may be from fewer or greater ECAPs.

Processing circuitry 214 then determines if the representative amplitude of the one or more respective ECAP is greater than the upper-bound of target ECAP adjustment window (940). As discussed herein, the target ECAP adjustment window may be defined by the target ECAP amplitude plus and minus a variance. Therefore, the target ECAP amplitude plus the variance may define the upper-bound of the target ECAP adjustment window. Similarly, the target ECAP amplitude minus the variance may define the lower-bound of the target ECAP adjustment window. In this manner, the target ECAP adjustment window may be determined so that adjustments are not made to the one or more parameters of the informed pulses for minor oscillations in the sensed ECAP amplitude. If processing circuitry 214 determines that the representative amplitude of the one or more ECAPs is greater than the target ECAP amplitude value plus the adjustment window ("YES" branch of block 940), processing circuitry 214 decreases the amplitude of the informed pulses and the control pulses by respective values (950). For example, the respective amplitudes of the informed pulses and the control pulses may be decreased by predetermined steps. As another example, the respective amplitudes of the informed pulses and the control pulses may be decreased by an amount proportional to the difference between the representative amplitude and the target ECAP amplitude. If processing circuitry 211 determines that the representative amplitude is less than the upper-bound of target ECAP adjustment window, ("NO" branch of block 940), processing circuitry 214 moves to block 960.

At block 960, processing circuitry 214 determines if the representative amplitude of the one or more respective ECAP is lesser than the lower-bound of target ECAP adjustment window. If the representative amplitude of the one or more respective ECAP is less than the lower-bound of target ECAP adjustment window (a "YES" branch of block 960), processing circuitry 214 increases the amplitude of the informed pulses and the control pulses by respective values (970). For example, the respective amplitudes of the informed pulses and the control pulses may be increased by predetermined steps. As another example, the respective amplitudes of the informed pulses and the control pulses may be increased by an amount proportional to the difference between the representative amplitude and the target ECAP amplitude. Processing circuitry 214 then continues to deliver an informed pulse and a control pulse according to the increased or decreased amplitudes. In some examples, the decrease or increase applied to the informed pulses and/or control pulses in steps 950 or 970 may apply to the amplitude or other parameter of the next scheduled informed pulse or control pulse. In this manner, even if a decrease is applied to the next informed pulse, the overall new amplitude of the next informed pulses may still be greater than the previous informed pulse if the scheduled amplitude of the next informed pulse minus the decrease is still greater than the amplitude of the previous informed pulse.

Although the process of operation 900 is described for adjusting the amplitude of the informed pulses and the control pulses, other parameter values may be changed in other examples. For example, sensed ECAP signals may be used to increase or decrease the pulse width of the informed pulse and the control pulse to adjust the amount of charge delivered to the tissue to maintain consistent volume of neural activation. In other examples, electrode combinations may be adjusted in order to deliver different amounts of charge and modify the number of neurons being recruited by each informed pulse. In other examples, processing circuitry 214 may be configured to adjust the slew rate of the informed pulses (i.e., the rate of change of the voltage and/or amplitude at the beginning and/or end of the pulse or each phase of the pulse) in response to a characteristic of the ECAP signal being greater than or less than the target ECAP adjustment window. For example, if the representative amplitude of the ECAP signal is greater than the upper-bound of the target ECAP adjustment window, processing circuitry 214 may decrease the slew rate of the next informed pulses (i.e., ramp up the amplitude of the pulse more slowly). If the representative amplitude of the ECAP signal is lower than the lower-bound of the target ECAP adjustment window, processing circuitry 214 may increase the slew rate of the next informed pulses (i.e., ramp up the amplitude of the pulse more quickly). The slew rate may contribute to the intensity of the pulse. Processing circuitry 214 may change one or more parameters defining the informed pulse according to the process of operation 900.

In other examples, processing circuitry 214 may perform operation 900 without adjusting the amplitude of the control pulses. In this manner, processing circuitry 214 may maintain the same amplitude of the control pulses and adjust the amplitude (or other parameter) in response to changes in the representative amplitude of the sensed ECAP signal(s) as compared to the last, or recent, representative amplitude of the sensed ECAP signal(s) to detect a change in the electrode-to-nerve distance. In other examples in which control pulses alone provide therapy for the patient, the technique of FIG. 9 may be employed by the system without adjusting or delivering any informed pulses.

Figure 10A:
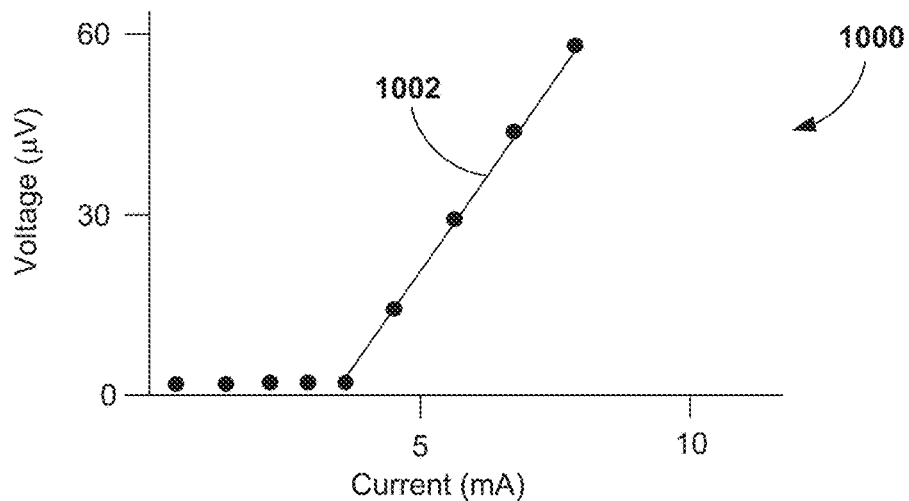
FIG. 10A is a graph of an example growth curve of sensed ECAPs from respective stimulation pulse amplitudes.

FIG. 10A is a graph 1000 of an example growth curve 1002 of sensed ECAPs from respective stimulation pulse amplitudes. Graph 1000 illustrates example ECAPs shown as dots for respective different current amplitudes of stimulation pulses. Typically, ECAPs will not be generated until the stimulation pulse amplitude reaches a threshold, approximately at 4.5 mA current in the example of FIG. 10A. Then, as the current amplitude is increased, the ECAP amplitude also increases approximately linearly. This linear relationship is shown by growth curve 1002. In the example of FIG. 10A, this slope may be approximately 32 µV/mA. However, the slope may vary for each patient based on the type of electrodes implanted, where the electrodes are implanted, the sensitivity of the patient's neurons to stimulation, neurological dysfunction, or other factors.

The slope of this growth curve that linearly increases may be referenced as the "gain" herein, as it indicates the relationship between sensed ECAP amplitudes and pulse amplitudes. Put another way, the gain value may represent the slope of the growth curve of values of the characteristic of ECAP signals (e.g., an amplitude such as the N1-P2 amplitude or the amplitude of any peak of the ECAP signal) elicited from respective calibration stimulation pulses delivered to the patient and at least partially defined by different values of a stimulation parameter (e.g., current amplitude, voltage amplitude, or pulse width). For example, the gain value for a patient may be used to dynamically adjust informed pulse amplitude and control amplitude based on the sensed ECAP amplitudes. In some examples, the gain may be approximated for a patient based on historical data for similar patients. In other examples, the system may generate a custom growth curve and gain specific to the patient before starting therapy with the system.

Figure 10B:
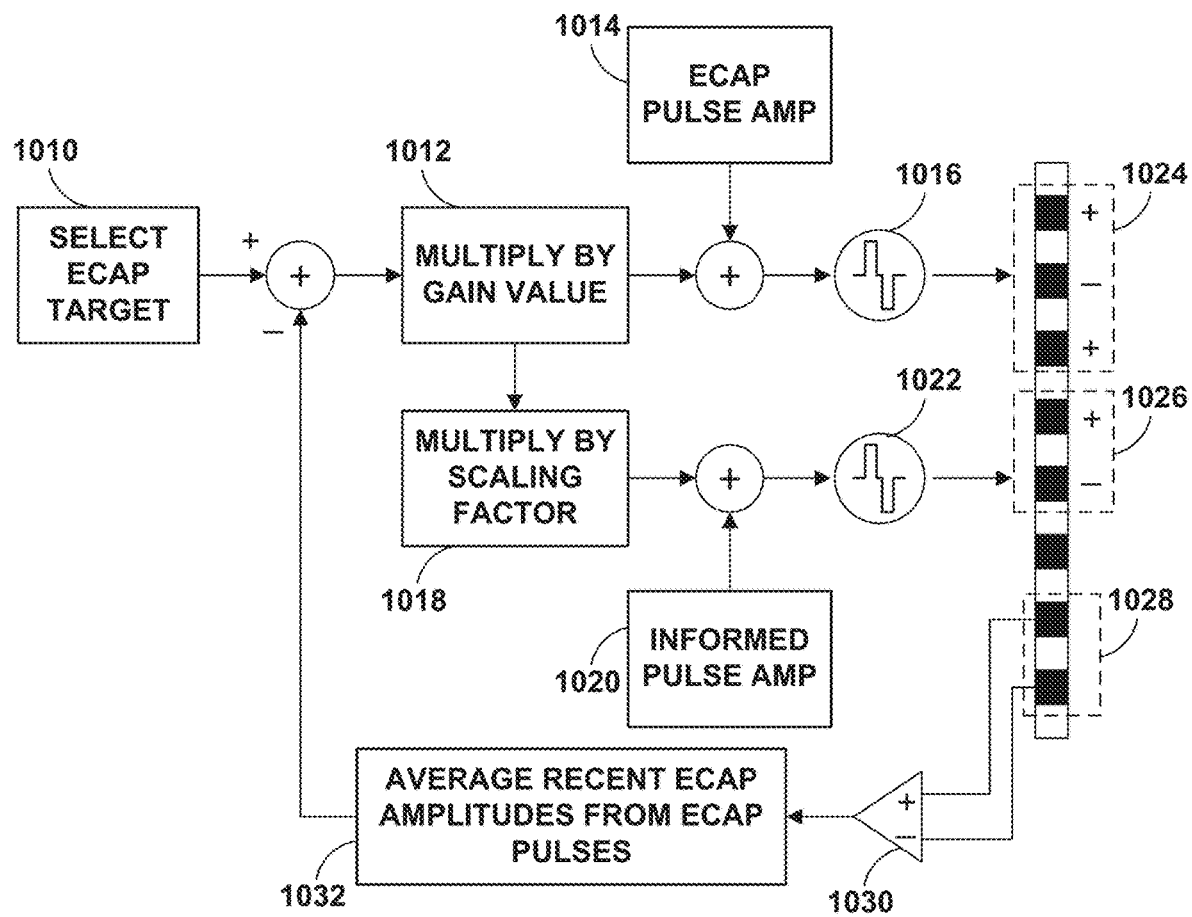
FIG. 10B is a diagram illustrating an example technique for adjusting stimulation therapy.

FIG. 10B is a diagram illustrating an example technique for adjusting stimulation therapy. As shown in the example of FIG. 10B, the system, such as IMD 200 or any other device or system described herein, may dynamically adjust informed pulse and control pulse amplitude (or other parameter) based on the gain value representing the patient sensitivity to stimulation. Processing circuitry 214 of IMD 200 may control stimulation generator 211 to deliver a control pulse to a patient. Processing circuitry 214 may then control sensing circuity 212 to sense an ECAP signal elicited by the control pulse and then identify a characteristic of the ECAP signal (e.g., an amplitude of the ECAP signal). Processing circuitry 214 may then determine, based on the characteristic of the ECAP signal and a gain value, a parameter value (e.g., an amplitude, pulse width value, pulse frequency value, and/or slew rate value) that at least partially defines an informed pulse. Processor 214 may then control stimulation generator 211 to deliver the informed pulse according to the determined informed pulse.

As shown in FIG. 10B, a control pulse 1016 is delivered to the patient via electrode combination 1024, shown as a guarded cathode of three electrodes. The resulting ECAP is sensed by the two electrodes at the opposing end of the lead of electrode combination 1028 fed to a differential amplifier 1030. For each sensed ECAP, processing circuitry 214 may measure an amplitude of a portion of the ECAP signal, such as the N1-P2 voltage amplitude from the portion of the ECAP signal. Processing circuitry 214 may average the recently measured ECAP amplitudes, such as averaging the most recent, and consecutive, 2, 3, 5, 5, 6, or more ECAP amplitudes. In some examples, the average may be a mean or median value. In some examples, one or more ECAP amplitudes may be ignored from the calculations if the amplitude value is determined to be an error. The measured amplitude (or average measured amplitude) is then subtracted from the selected target ECAP amplitude 1010 to generate a differential amplitude. The selected target ECAP amplitude 1010 may be determined from an ECAP sensed when the physician or patient initially discovers effective therapy from the informed pulses. This target ECAP amplitude 1010 may essentially represent a reference distance between the stimulation electrodes and the target neurons (e.g., the spinal cord for the case of SCS).

The differential amplitude is then multiplied by the gain value for the patient to generate a preliminary differential value 1012. The preliminary differential value is added to the ECAP pulse amplitude (e.g., the control pulse amplitude) to generate the new, or adjusted, ECAP pulse amplitude that at least partially defines the next control pulse 1016.

To adjust the informed pulse amplitude, the differential value is multiplied by a scaling factor 1018 to generate the therapy differential value. For example, the scaling factor may be the ratio of the previously delivered informed pulse amplitude to the previously delivered control pulse amplitude. The therapy differential value is then added to the previously delivered informed pulse amplitude 1020 to generate the new, or adjusted, informed pulse amplitude that at least partially defines the next informed pulse 1022. This process can be applied to the informed pulses from multiple stimulation programs. For example, if informed pulses from two different stimulation programs are delivered as a part of stimulation therapy, the system may multiply the respective scaling factors by the differential value to obtain a respective therapy differential value for the informed pulses of each stimulation program. The next informed pulse 1022 (or pulses if multiple stimulation programs are involved in therapy) is then delivered, interleaved with control pulse 1016, to the patient via electrode combination 1026. In some examples, at least two control pulses may be delivered, and at least two respective ECAP signals sensed, between consecutive informed pulses. This increased frequency of control pulses may allow the system to quickly adjust informed pulse amplitudes for any changes in the distance between electrodes and neurons. Although electrode combination 1026 is different than electrode combinations 1024 and 1028, electrode combination 1026 can be any set of electrodes on the lead as desired for therapy because the informed pulse is delivered in a non-overlapping fashion with control pulses and sensed ECAP signals. In some examples, a next control pulse or informed pulse may be scheduled to have an amplitude (or other parameter) that is higher or lower than the previous informed pulse or control pulse. Therefore, the system may apply the differential value for the control pulse and/or informed pulse to the scheduled amplitude (or other parameter) of the next control pulse and/or the informed pulse instead of just applying the respective differential value to the previous amplitude or other parameter of the previous control pulse or informed pulse.

In some examples, the pulse width of the informed pulse may be greater than approximately 300 μs and less than approximately 1000 μs. In other examples, the pulse width of the informed pulse may be less than approximately 300 μs or greater than 1000 μs. The informed pulse may be a monophasic pulse followed a passive recharge phase. However, in other examples, the informed pulse may be a bi-phasic pulse that includes a positive phase and a negative phase. In some examples, the control pulse width may be less than approximately 300 μs. In some examples, the control pulse is a bi-phasic pulse including a positive phase and a negative phase. For example, a bi-phasic control pulse may include a positive phase having a duration of approximately 100 μs, a negative phase having a duration of approximately 100 μs, and an interphase interval of an approximately 30 μs duration. In this manner, the control pulse may be completed prior to detection of the resulting ECAP signal. In some examples, an informed pulse may be less than 300 μs, but the following passive recharge phase or even an active recharge phase (of a bi-phasic pulse) may still obscure the detectable ECAP signal from that informed pulse. In addition, regardless of the pulse width of the informed pulse, it may be beneficial to sense ECAP signals resulting from control pulses so that the informed pulses can have parameter values (e.g., amplitude, pulse width, frequency, pulse shape, electrode combination, etc.) that would otherwise interfere with the sensing of the resulting ECAP signal or the production of a detectable ECAP signal.

In one example of FIG. 10B, multiple stimulation programs may define informed pulses that are informed from the ECAP signal detected from a control pulse. For example, with a lead having eight electrodes labeled 1-8, the control pulse may be initially delivered at 10.0 milliamps (mA) with pulse width of 210 μs (a positive phase of 90 μs, an interphase interval of 30 μs, and a negative phase of 90 μs). The control pulse may be delivered with a guarded cathode configuration with the cathode on electrode 7 and anodes on electrodes 6 and 8 on either side of electrode 7. One stimulation program may define a first informed pulse of 4.0 mA with a pulse width of 800 μs (a positive phase of 400 μs a negative phase of 400 μs) having a cathode on electrode 6 and an anode on electrode 4. Another stimulation program may define a second informed pulse of 5.0 mA with a pulse width of 400 μs (a positive phase of 200 μs a negative phase of 200 μs) having a cathode on electrode 2 and an anode on electrode 3. The first and second informed pulses may be interleaved over time, and both of the first and second informed pulses from each respective stimulation program may be adjusted, or informed, based on the ECAP signal detected from the control pulse and the scaling factor, or ratio, for each of the first and second informed pulses with respect to the control pulse. For example, the scaling factor for the first informed pulse may be 40% (e.g., 4.0 mA divided by 10 mA) and the scaling factor for the second informed pulse may be 50% (e.g., 5.0 mA divided by 10 mA). Therefore, if the determined differential value 1012 of 2 mA is determined to be added for the next the control pulse, the system would determine that the next first informed pulse from the first stimulation program should be increased by 0.8 mA (to 4.8 mA) and the next second informed pulse from the second stimulation program should be increased by 1.0 mA (to 6.0 mA). In this manner, the system may adjust informed pulses from two or more stimulation programs based on the ECAP signal detected from a single control pulse.

Although the technique of FIG. 10B is described for adjusting the amplitude of the informed pulses and the control pulses, other parameter values may be changed in other examples. For example, sensed ECAP signals may be used to increase or decrease the pulse width of the informed pulse and the control pulse to adjust the amount of charge delivered to the tissue to maintain consistent volume of neural activation. In other examples, electrode combinations may be adjusted in order to deliver different amounts of charge and modify the number of neurons being recruited by each informed pulse. In other examples, processing circuitry 214 may be configured to adjust the slew rate of the informed pulses and/or control pulses (i.e., the rate of change of the voltage and/or amplitude at the beginning and/or end of the pulse or each phase of the pulse) in response to a characteristic of the ECAP signal, such as the amplitude of recent ECAP amplitudes. For parameters other than amplitude, gain values may need to be determined that are specific for each type of parameter in order to appropriately adjust that type of parameter. Processing circuitry 214 may change one or more parameters defining the informed pulse and/or control pulse according to the process FIG. 10B. For example, the ECAP signal may be used to control multiple concurrent feedback mechanisms simultaneously for respective pulse parameters. In other examples, processing circuitry 214 may switch between two or more feedback mechanisms when processing circuitry 214 reaches a limit of adjustment for a specific parameter. For example, processing circuitry 214 may be configured to use a feedback control mechanism to adjust amplitude as long as the amplitude remains within a range (e.g., a range defined by the clinician) and then switch to a different feedback control mechanism to adjust a different parameter (e.g., pulse width or slew rate) of the informed pulses and/or control pulses in response to the amplitude exceeding the range.

In other examples, processing circuitry 214 may perform the technique of FIG. 10B without adjusting the amplitude of the control pulses. In this manner, processing circuitry 214 may maintain the same amplitude of the control pulses and adjust the amplitude (or other parameter) of the informed pulses in response to changes in the average amplitude of the sensed ECAP signal(s) as compared to the last, or recent, average amplitude of the sensed ECAP signal(s) to detect a change in the electrode-to-nerve distance. In this case, the target ECAP amplitude 1010 may be adjusted by the difference between the target ECAP amplitude and the most recent sensed ECAP amplitude (or averaged amplitudes), for example. In other examples in which control pulses alone provide therapy for the patient, the technique of FIG. 10B may be employed by the system without adjusting or delivering any informed pulses.

Figure 11:
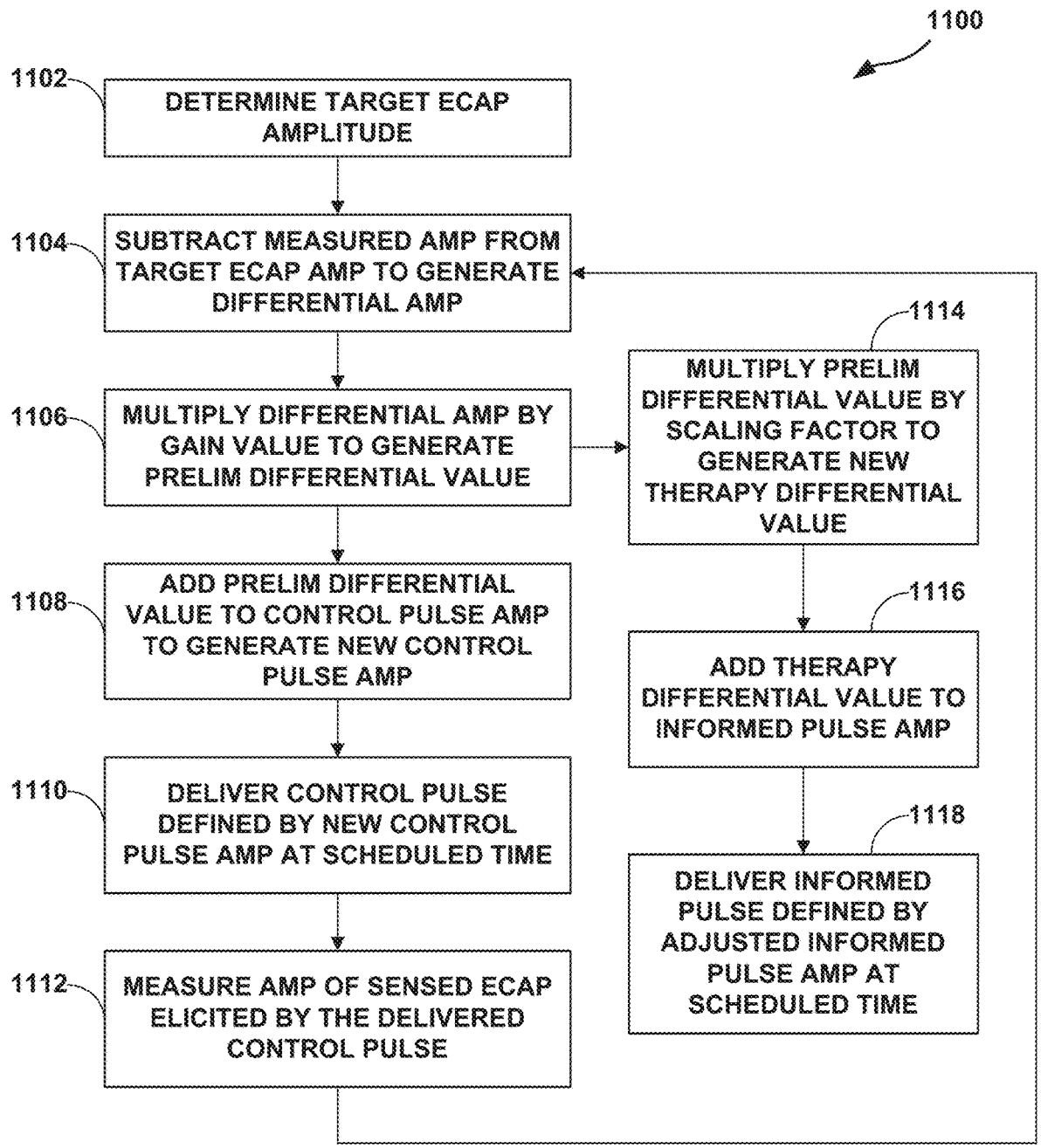
FIG. 11 is a flowchart illustrating an example technique for adjusting stimulation therapy.

FIG. 11 is a flowchart illustrating an example operation 1100 for adjusting stimulation therapy. IMD 200 and processing circuitry 214 will be described in the example of FIG. 11, but other IMDs such as IMD 110 or other devices or systems may perform, or partially perform, operation 1100. Operation 1100 may be similar to the diagram and discussion related to FIG. 10B.

In the example of FIG. 11, processing circuitry 214 determines the target ECAP amplitude (1102). The target ECAP amplitude may be determined based on sample stimulation initially delivered to the patient. The target ECAP amplitude may be the N1-P2 amplitude of the ECAP signal, but other measures of amplitude, such as amplitude of one or more different peaks in the ECAP signal may be used instead. Alternatively, the target ECAP amplitude may instead be a different characteristic of the ECAP signal such as the area under one or more peaks of the ECAP signal, frequency content of the ECAP signal, maximum and/or minimum peak timing of the ECAP signal, or any other characteristic of the ECAP signal. In some examples, processing circuitry 214 is configured to automatically change the target ECAP amplitude over a period of time according to a predetermined function (e.g., a sinusoid function) in order to change the volume of neuron activation and, in some examples, the perceived sensation of the informed pulses.

Processing circuitry 214 receives a measured amplitude from the previously sensed ECAP signal. In order to use the ECAP signal as feedback to control the informed pulses of electrical stimulation therapy for the patient, processing circuitry 214 subtracts the measured amplitude from the target ECAP amplitude to generate a differential amplitude (1104). In some examples, or as additional measured amplitudes are available from the process, processing circuitry 214 may average a certain number of recent measured amplitudes (e.g., two or more) to create a rolling average of measured ECAP amplitudes and subtract the average measured amplitudes from the target ECAP amplitude to smooth out variations between ECAP signals. The differential amplitude is thus a representation of how much the electrodes have moved relative to the neurons and can be used to adjust the amplitudes of the informed pulses and the control pulses to maintain consistent volume of neural activation of the neurons that provide relief to the patient.

Processing circuitry 214 then multiplies the differential amplitude by a gain value for the patient to generate a preliminary differential value (1106). The gain value may represent the slope of the growth curve for the patient. Processing circuitry 214 then uses the preliminary differential value to adjust the amplitudes of both subsequent informed pulses and control pulses (e.g., the ECAP test pulses). Processing circuitry 214 adds the preliminary differential value to the control pulse amplitude to generate a new control pulse amplitude (1108). Processing circuitry 214 then controls stimulation generator 211 to deliver a subsequent control pulse defined by the new control pulse amplitude at a scheduled time, such as according to the frequency of the control pulses or according to the next available window between informed pulses (1110). Processing circuitry 214 also controls sensing circuitry 212 to measure the amplitude of the sensed ECAP elicited by the recently delivered control pulse (1112) to use again as feedback in block 1104.

In addition to adjusting the amplitude of the control pulses, processing circuitry 214 uses the preliminary amplitude to adjust the informed pulse amplitude. Processing circuitry 214 multiplies the differential value by a scaling factor to generate a new therapy differential value (1114). The scaling factor may be determined as the ratio between the amplitude of the most recently delivered informed pulse and the amplitude of the most recently delivered control pulse that elicited the ECAP signal used to generate the measured amplitude used in block 1104. The scaling factor may scale up the differential amplitude for the informed pulses because the differential amplitude was generated based on amplitudes of control pulses. Processing circuitry 214 then adds the therapy differential value to the most recent informed pulse amplitude to generate a new informed pulse amplitude (1116). Processing circuitry 214 then controls stimulation generator 211 to deliver the next informed pulse with the newly adjusted informed pulse amplitude at the scheduled time according to the predetermined pulse frequency of the informed pulses (1118).

Although operation 1100 is described for adjusting the amplitude of informed pulses and control pulses, a similar operation may be used to adjust other stimulation parameters in other examples. For example, parameters that contribute to the intensity of the informed pulses and control pulses may affect the volume of neural activation, such as pulse width, pulse frequency, or even pulse shape (e.g., the amount of charge per pulse). Therefore, processing circuitry 214 may adjust a different parameter instead of, or in addition to, amplitude using the sensed ECAP signal elicited from the control pulses. For example, processing circuitry 214 may increase the pulse width of the informed pulses and control pulses in response to detecting a decreased ECAP amplitude.

Figure 12:
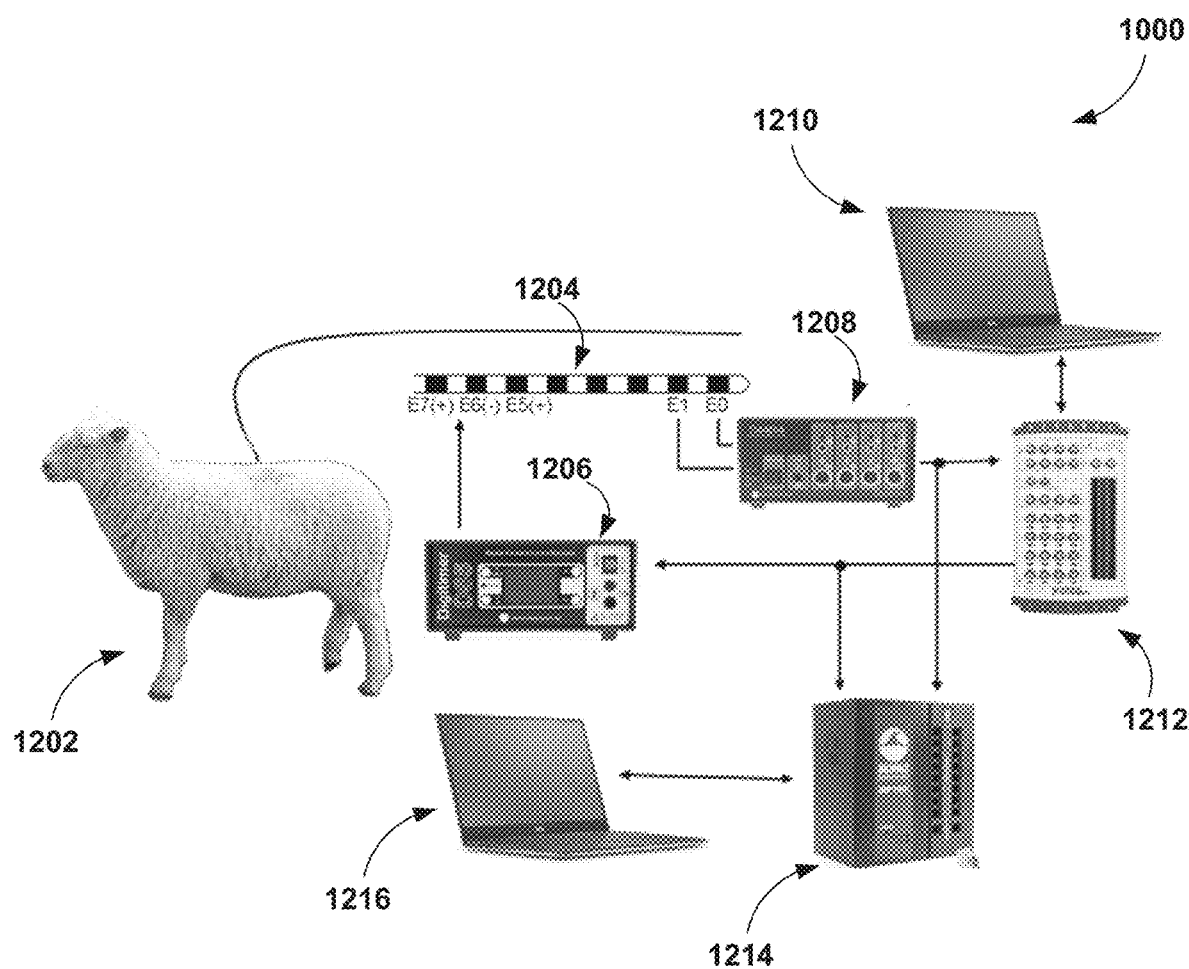
FIG. 12 is a diagram of example equipment used in an experiment testing the efficacy of a feedback mechanism using sensed ECAPs.

FIG. 12 is a diagram of example equipment used in an experiment testing the efficacy of a feedback mechanism using sensed ECAPs. As shown in FIG. 12, system 1000 may include a lead 1204, stimulation generator 1206, ECAP amplifier 1208, feedback control device 1210, signal digitizer 1212, analog-to-digital converter 1214, and data storage device 1216. Feedback control device 1210 may control stimulation generator 1206 to deliver stimulation pulses (e.g., control pulses) to the patient 1202 (e.g., a sheep) via electrodes on lead 1204. ECAP amplifier 1208 senses the resulting ECAP signal which is digitized and stored in data storage device 1216 for later review. In addition, the ECAP signal is received by feedback control device 1210 and used to measure the ECAP amplitude and adjust the control pulses according to a feedback control mechanism such as the feedback mechanism described in FIGS. 10B and 11, for example. This experimental setup of FIG. 12 may be used to evaluate the efficacy of the feedback control mechanism, as shown in the graphs of FIG. 13.

Figure 13:
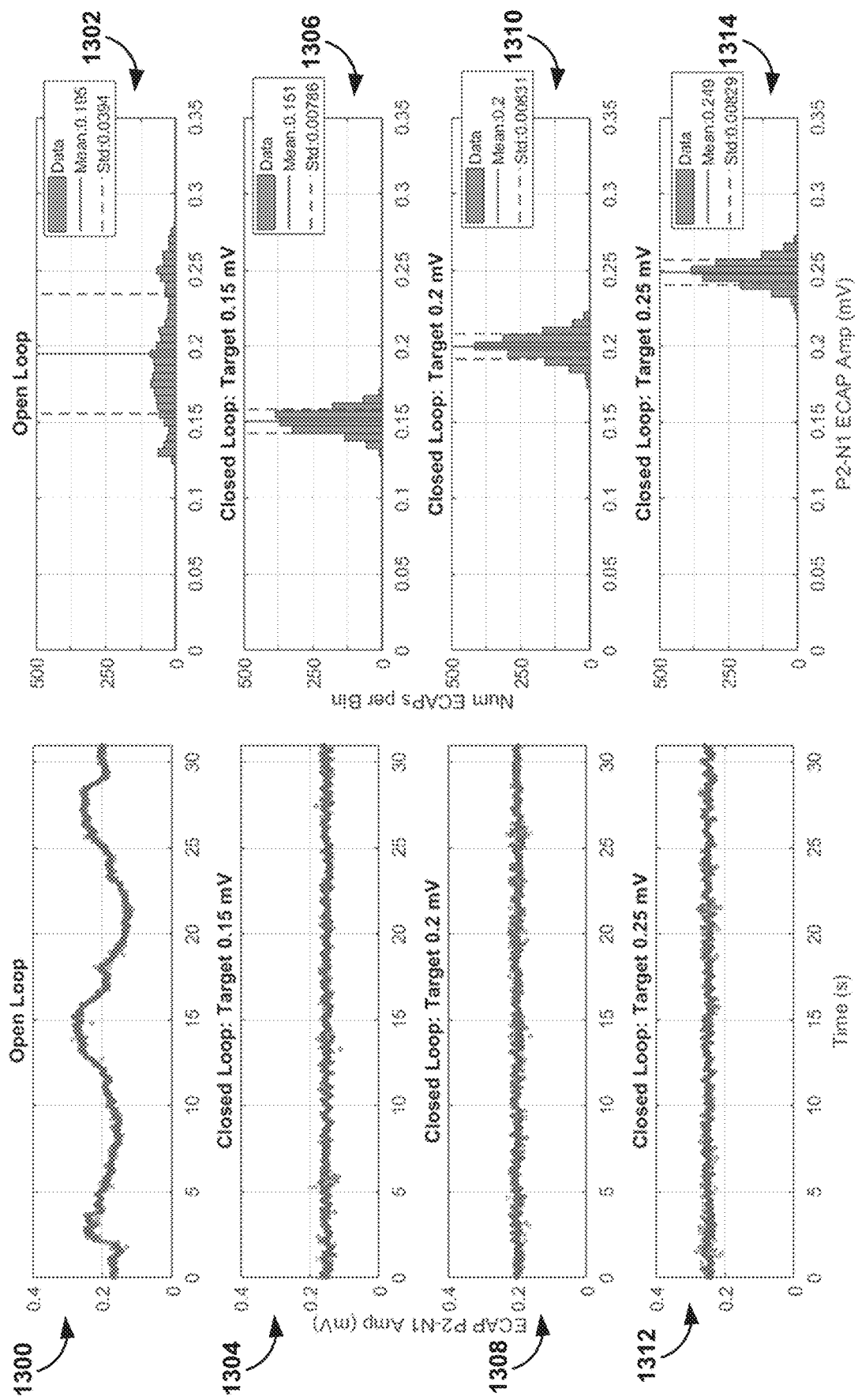
FIG. 13 includes graphs of sensed ECAP voltage amplitudes using open loop and different feedback target amplitudes in a closed loop configuration.

FIG. 13 includes graphs of sensed ECAP voltage amplitudes using a feedback mechanism in the experiment described in FIG. 12. As shown in FIG. 13, graphs 1300, 1304, 1308, and 1312 illustrate the measured N1-P2 amplitudes of ECAP signals detected over time. Graphs 1302, 1306, 1310, and 1314 group similar N1-P2 amplitudes together to illustrate how closely grouped, or how spread apart, the measured N1-P2 amplitudes are from each other. More consistent, or closely grouped, measured amplitudes from ECAP signals indicates that the feedback mechanism is maintaining the target ECAP amplitude and providing consistent volume of neural activation for the patient (e.g., the sheep of FIG. 12).

Graphs 1300 and 1302 illustrate how the measured ECAP amplitude changes over time in open loop, or when no feedback mechanism is employed to adjust the amplitude of the control pulses. In other words, the measured ECAP amplitude varies as the sheep moves because the electrode-to-neuron distance is changing. In contrast, employing feedback mechanisms results in graphs 1304 and 1306 indicating ECAP amplitudes for a target ECAP amplitude of 0.15 mV, graphs 1308 and 1310 indicating ECAP amplitudes for a target ECAP amplitude of 0.20 mV, and graphs 1312 and 1314 indicating ECAP amplitudes for a target ECAP amplitude of 0.25 mV. As shown in these graphs where feedback mechanism is employed to control pulse amplitude, the ECAP amplitude remains relatively consistent over time with minimal variation as compared to open loop delivery. These graphs indicate that feedback control mechanisms described herein may be effective at maintaining consistent volume of neural activation that may result in consistent therapy efficacy for the patient even during patient movement and activity.

The following examples are examples systems, devices, and methods described herein. Example 1: A method comprising: delivering electrical stimulation therapy to a patient, the electrical stimulation therapy comprising a plurality of informed pulses at a predetermined pulse frequency over a period of time, wherein the plurality of informed pulses are at least partially defined by a first set of parameter values; delivering, over the period of time, a plurality of control pulses interleaved with at least some informed pulses of the plurality of informed pulses, wherein the plurality of control pulses are at least partially defined by a second set of parameter values different than the first set of parameter values; sensing, after one or more control pulses of the plurality of control pulses and prior to an immediately subsequent informed pulse of the plurality of informed pulses, a respective evoked compound action potential (ECAP); adjusting, based on at least one respective ECAP, one or more parameter values of the first set of parameter values that at least partially defines the plurality of informed pulses of the electrical stimulation therapy; an delivering the electrical stimulation therapy to the patient according to the adjusted one or more parameter values of the first set of parameter values.

Example 2: the method of example 1, wherein the pulse width of each informed pulse of the plurality of informed pulses is greater than approximately 300 microseconds and less than approximately 1000 microseconds.

Example 3: the method of any combination of examples 1-2, wherein the frequency of the plurality of informed pulses is less than approximately 400 Hertz.

Example 4: the method of any combination of examples 1-3, wherein the pulse width of each control pulse of the plurality of control pulses is less than approximately 300 microseconds.

Example 5: the method of any combination of examples 1-4, wherein delivering the plurality of control pulses comprises: delivering one control pulse of the plurality of control pulses during each time event of a plurality of time events; wherein each time event of the plurality of time events comprises a time between consecutive informed pulses of the plurality of informed pulses at the predetermined pulse frequency over the period of time.

Example 6: the method of any combination of examples 1-5, wherein delivering the plurality of control pulses comprises: delivering two or more control pulses of the plurality of control pulses during each time event of a plurality of time events, wherein each time event of the plurality of time events comprises a time between consecutive informed pulses of the plurality of informed pulses at the predetermined pulse frequency over the period of time.

Example 7: the method of any combination of examples 1-6, further comprising, for each sensed respective ECAP: determining a representative amplitude of at least one respective ECAP; and comparing the representative amplitude of the at least one respective ECAP to a target ECAP amplitude, wherein adjusting the one or more parameter values comprises adjusting, based on the comparison of the representative amplitude to the target ECAP amplitude, the one or more parameter values.

Example 8: the method of any combination of examples 1-7, further comprising: responsive to determining that the representative amplitude is greater than an upper-bound of a target ECAP adjustment window, decreasing the amplitude of one or more informed pulses of the plurality of informed pulses following the at least one respective ECAP; and responsive to determining that the representative amplitude is greater than an upper-bound of a target ECAP adjustment window, decreasing the amplitude of one or more control pulses of the plurality of control pulses following the at least one respective ECAP.

Example 9: the method of any combination of examples 1-8, further comprising: responsive to determining that the representative amplitude is less than a lower-bound of the target ECAP adjustment window, increasing the amplitude of one or more informed pulses of the plurality of informed pulses following the at least one respective ECAP; and responsive to determining that the representative amplitude is less than a lower-bound of the target ECAP adjustment window, increasing the amplitude of one or more control pulses of the plurality of control pulses following the at least one respective ECAP.

Example 10: the method of any combination of examples 1-9, further comprising, for each sensed respective ECAP: determining an amplitude of the respective ECAP; and determining a percentage difference between the amplitude of the respective ECAP and a target ECAP amplitude, wherein adjusting the one or more parameter values comprises changing an amplitude value of subsequent informed pulses to be inversely proportional to the percentage difference between the amplitude of the respective ECAP and the target ECAP amplitude.

Example 11: the method of any combination of examples 1-10, further comprising: receiving, from a sensor, a signal indicating that the activity level of the patient has changed; and in response to receiving the signal, one of increasing or decreasing the frequency of the plurality of control pulses delivered to the patient.

Example 12: the method of any combination of examples 1-11, wherein each informed pulse of the plurality of informed pulses is a monophasic pulse followed by a passive recharge phase, and wherein each control pulse of the plurality of control pulses is a bi-phasic pulse comprising a positive phase and a negative phase.

Example 13: the method of any combination of examples 1-12, wherein each informed pulse of the plurality of informed pulses is a first bi-phasic pulse comprising a first positive phase and a first negative phase, and wherein each control pulse of the plurality of control pulses is a second bi-phasic pulse comprising a second positive phase and a second negative phase.

Example 14: the method of any combination of examples 1-13, wherein the plurality of control pulses comprise a plurality of non-therapeutic pulses, and wherein the plurality of informed pulses comprise a plurality of therapy pulses.

Example 15: a system comprising: stimulation generation circuitry configured to: deliver electrical stimulation therapy to a patient, wherein the electrical stimulation therapy comprises a plurality of informed pulses at a predetermined pulse frequency over a period of time, and wherein the plurality of informed pulses are at least partially defined by a first set of parameter values, and deliver a plurality of control pulses over the period of time, wherein the plurality of control pulses is interleaved with at least some informed pulses of the plurality of informed pulses, and wherein the plurality of control pulses are at least partially defined by a second set of parameter values different than the first set of parameter values; and processing circuitry configured to: receive a sensed respective evoked compound action potential (ECAP) after one or more control pulses of the plurality of control pulses and prior to a subsequent informed pulse of the plurality of informed pulses, adjust, based on at least one respective ECAP, one or more parameter values of the first set of parameter values that at least partially define the plurality of informed pulses of the electrical stimulation therapy, and deliver, via the stimulation generation circuitry, the electrical stimulation therapy to the patient according to the adjusted one or more parameter values of the first set of parameter values.

Example 16: the system of example 15, wherein the pulse width of each informed pulse of the plurality of informed pulses is greater than approximately 300 microseconds and less than approximately 1000 microseconds.

Example 17: the system of any combination of examples 15-16, wherein the predetermined pulse frequency of the plurality of informed pulses is less than approximately 400 Hertz.

Example 18: the system of any combination of examples 15-17, wherein the pulse width of each control pulse of the plurality of control pulses is less than approximately 300 microseconds.

Example 19: the system of any combination of examples 15-18, wherein the stimulation generator is further configured to: deliver one control pulse of the plurality of control pulses during each time event of a plurality of time events, wherein each time event of the plurality of time events comprises a time between consecutive informed pulses of the plurality of informed pulses at the predetermined pulse frequency over the period of time.

Example 20: the system of any combination of examples 15-19, wherein the stimulation generator is further configured to: deliver two or more control pulses of the plurality of control pulses during each time event of a plurality of time events, wherein each time event of the plurality of time events comprises a time between consecutive informed pulses of the plurality of informed pulses at the predetermined pulse frequency over the period of time.

Example 21: the system of any combination of examples 15-20, wherein the one or more parameter values comprise at least one of: pulse amplitude, pulse width, pulse frequency, and pulse shape.

Example 22: the system of any combination of examples 15-21, further comprising: a target ECAP amplitude and an ECAP adjustment window ranging from a lower-bound to an upper-bound, wherein the target ECAP amplitude is within the ECAP adjustment window, and wherein the one or more processors are further configured to: determine an amplitude of the respective ECAP after each of the one or more control pulses of the plurality of control pulses; and calculate a representative amplitude of at least one respective ECAP.

Example 23: the system of any combination of examples 15-22, wherein the one or more processors are further configured to: decrease, if the representative amplitude is greater than the upper-bound of the ECAP adjustment window, the amplitude of one or more informed pulses of the plurality of the informed pulses following the at least one respective ECAP; and decrease, if the representative amplitude is greater than an upper-bound of a target ECAP adjustment window, the amplitude of one or more control pulses of the plurality of control pulses following the at least one respective ECAP.

Example 24: the system of any combination of examples 15-23, wherein the one or more processors are further configured to: increase, if the representative amplitude is less than the lower-bound of the ECAP adjustment window, the amplitude of one or more informed pulses of the plurality of informed pulses following the at least one respective ECAP; and increase, if the representative amplitude is less than a lower-bound of the target ECAP adjustment window, the amplitude of one or more control pulses of the plurality of control pulses following the at least one respective ECAP.

Example 25: the system of any combination of examples 15-24, further comprising: a sensor; and wherein the one or more processors are further configured to: receive, from the sensor, a signal indicating that the activity level of the patient has changed; and in response to receiving the signal, one of increase or decrease the frequency of the plurality of control pulses delivered to the patient via the stimulation generation circuitry.

Example 26: the system of any combination of examples 15-25, wherein each informed pulse of the plurality of informed pulses is a monophasic pulse followed by a passive recharge phase, and wherein each control pulse of the plurality of control pulses is a bi-phasic pulse.

Example 27: the system of any combination of examples 15-26, further comprising: a memory configured to store a target ECAP amplitude and an ECAP adjustment window; and one or more electrodes, wherein the stimulation generation circuitry is further configured to: deliver electrical stimulation therapy to the patient via the one or more electrodes, and deliver the plurality of control pulses to the patient via the one or more electrodes.

Example 28: the system of any combination of examples 15-27, wherein the plurality of control pulses comprise a plurality of non-therapeutic pulses, and wherein the plurality of informed pulses comprise a plurality of therapy pulses.

Example 29: a computer-readable storage medium comprising instructions that, when executed, cause one or more processors to: control delivery of electrical stimulation therapy to a patient, the electrical stimulation therapy comprising a plurality of informed pulses at a predetermined pulse frequency over a period of time, wherein the plurality of informed pulses are at least partially defined by a first set of parameter values; control, over the period of time, delivery of a plurality of control pulses interleaved with at least some informed pulses of the plurality of informed pulses, wherein the plurality of control pulses are at least partially defined by a second set of parameter values different than the first set of parameter values; receive, after one or more control pulses of the plurality of control pulses and prior to an immediately subsequent informed pulse of the plurality of informed pulses, a sensed respective evoked compound action potential (ECAP); adjust, based on at least one respective ECAP, one or more parameter values of the first set of parameter values that at least partially define the plurality of informed pulses of the electrical stimulation therapy; and control delivery of the electrical stimulation therapy to the patient according to the adjusted one or more parameter values of the first set of parameter values.

Example 30: a method comprising: delivering a control stimulation pulse to a patient, the control stimulation pulse having a first pulse width; sensing an evoked compound action potential (ECAP) signal elicited by the control stimulation pulse; identifying a characteristic of the ECAP signal; determining, based on the characteristic of the ECAP signal and a gain value, a therapy parameter value that at least partially defines an informed stimulation pulse from a plurality of informed pulses, wherein the plurality of informed pulses have a second pulse width longer than the first pulse width; and delivering the informed stimulation pulse according to the determined therapy parameter value.

Example 31: the method of example 30, wherein the gain value represents a slope of a growth curve of values of the characteristic of ECAP signals elicited from respective calibration stimulation pulses delivered to the patient and at least partially defined by different values of a stimulation parameter.

Example 32: the method of any combination of examples 30-31, wherein the characteristic of the ECAP signal is a measured amplitude of a portion of the ECAP signal, wherein the therapy parameter value comprises a new informed amplitude value, and wherein determining the new informed amplitude value comprises: subtracting the measured amplitude from a target ECAP amplitude value for the patient to generate a differential amplitude; multiplying the differential amplitude by the gain value to generate a preliminary differential value; multiplying the preliminary differential value by a scaling factor to generate an informed differential value, wherein the scaling factor represents a ratio of a previous informed amplitude value that defines a previous informed stimulation pulse delivered prior to the control stimulation pulse to a control amplitude value defining the control stimulation pulse; and adding the informed differential value to the previous informed amplitude value to generate the new informed amplitude value that at least partially defines the informed stimulation pulse.

Example 33: the method of any combination of examples 30-32, wherein the control pulse is a first control pulse, and wherein the method further comprises generating a new control amplitude value defining a second control stimulation pulse by adding the preliminary differential value to a previous control amplitude value defining the first control stimulation pulse, the second control stimulation pulse to be delivered to the patient subsequent to delivery of the first control stimulation pulse.

Example 34: the method of any combination of examples 30-33, wherein the informed stimulation pulse is a first informed stimulation pulse, and wherein the method further comprises delivering, after delivery of the first informed stimulation pulse, a second informed stimulation pulse at least partially defined by the new informed amplitude value.

Example 35: the method of any combination of examples 30-34, wherein the measured amplitude of the portion of the ECAP signal comprises a voltage amplitude between an N1 peak and a P2 peak of the ECAP signal.

Example 36: the method of any combination of examples 30-35, wherein determining, based on the characteristic of the ECAP signal and the gain value, the therapy parameter value that at least partially defines the informed stimulation pulse comprises: determining, based on an average value of the characteristic of a plurality of consecutively sensed ECAP signals and the gain value, the therapy parameter value that at least partially defines the informed stimulation pulse, the plurality of consecutively sensed ECAP signals comprising the ECAP signal.

Example 37: the method of any combination of examples 30-36, wherein a plurality of control stimulation pulses comprises the control stimulation pulse, wherein a plurality of informed stimulation pulses comprises the informed stimulation pulse, and wherein the method further comprises interleaving the plurality of control stimulation pulses with at least some of the plurality of informed stimulation pulses.

Example 38: the method of any combination of examples 30-37, wherein interleaving the plurality of control stimulation pulses within at least some of the plurality of informed stimulation pulses comprises: delivering at least two control stimulation pulses of the plurality of control stimulation pulses between consecutive informed stimulation pulses;

and sensing, between the consecutive informed stimulation pulses, at least two ECAP signals elicited by respective control stimulation pulses of the at least two control stimulation pulses.

Example 39: the method of any combination of examples 30-38, wherein a pulse width of the informed stimulation pulse is greater than approximately 300 microseconds and less than approximately 1000 microseconds.

Example 40: the method of any combination of examples 30-39, wherein a pulse width of the control stimulation pulse is less than approximately 300 microseconds.

Example 41: the method of any combination of examples 30-40, wherein the informed stimulation pulse is a monophasic pulse followed by a passive recharge phase, and wherein the control stimulation pulse is a bi-phasic pulse comprising a positive phase and a negative phase.

Example 42: the method of any combination of examples 30-41, wherein the informed stimulation pulse is a first bi-phasic pulse comprising a first positive phase and a first negative phase, and wherein the control stimulation pulse is a second bi-phasic pulse comprising a second positive phase and a second negative phase.

Example 43: the method of any combination of examples 30-42, wherein the plurality of control stimulation pulses comprise a plurality of non-therapeutic pulses, and wherein the plurality of informed pulses comprise a plurality of therapy pulses.

Example 44: A system comprising: stimulation generation circuitry configured to: deliver a control stimulation pulse to a patient, the control stimulation pulse having a first pulse width; and deliver an informed stimulation pulse from a plurality of informed pulses and according to a therapy parameter value, wherein the plurality of informed pulses have a second pulse width longer than the first pulse width; and processing circuitry configured to: receive a sensed evoked compound action potential (ECAP) signal elicited by the control stimulation pulse; identify a characteristic of the ECAP signal; and determine, based on the characteristic of the ECAP signal and a gain value, the therapy parameter value that at least partially defines the informed stimulation pulse.

Example 45: the method of example 44, wherein the gain value represents a slope of a growth curve of values of the characteristic of ECAP signals elicited from respective calibration stimulation pulses delivered to the patient and at least partially defined by different values of a stimulation parameter.

Example 46: the system of any combination of examples 44-45, wherein the characteristic of the ECAP signal is a measured amplitude of a portion of the ECAP signal, wherein the therapy parameter value comprises a new informed amplitude value, and wherein the processing circuitry is configured to determine the new therapy parameter value by: subtracting the measured amplitude from a target ECAP amplitude value for the patient to generate a differential amplitude; multiplying the differential amplitude by the gain value to generate a preliminary differential value; multiplying the preliminary differential value by a scaling factor to generate an informed differential value, wherein the scaling factor represents a ratio of a previous informed amplitude value that defines a previous informed stimulation pulse delivered prior to the control stimulation pulse to a control amplitude value defining the control stimulation pulse; and adding the informed differential value to the previous informed amplitude value to generate the new informed amplitude value that at least partially defines the informed stimulation pulse.

Example 47: the system of any combination of examples 44-46, wherein the control pulse is a first control pulse, and wherein the processing circuitry is configured to generate a new control amplitude value defining a second control stimulation pulse by adding the preliminary differential value to a previous control amplitude value defining the first control stimulation pulse, the second control stimulation pulse to be delivered to the patient subsequent to delivery of the first control stimulation pulse.

Example 48: the system of any combination of examples 44-47, wherein the informed stimulation pulse is a first informed stimulation pulse, and wherein the processing circuitry is configured to control the stimulation generation circuitry to deliver, after delivery of the first informed stimulation pulse, a second informed stimulation pulse at least partially defined by the new informed amplitude value.

Example 49: the system of any combination of examples 44-48, wherein the measured amplitude of the portion of the ECAP signal comprises a voltage amplitude between an N1 peak and a P2 peak of the ECAP signal.

Example 50: the system of any combination of examples 44-49, wherein the processing circuitry is configured to determine, based on the characteristic of the ECAP signal and the gain value, the therapy parameter value that at least partially defines the informed stimulation pulse by: determining, based on an average value of the characteristic of a plurality of consecutively sensed ECAP signals and the gain value, the therapy parameter value that at least partially defines the informed stimulation pulse, the plurality of consecutively sensed ECAP signals comprising the ECAP signal.

Example 51: the system of any combination of examples 44-50, wherein a plurality of control stimulation pulses comprises the control stimulation pulse, wherein a plurality of informed stimulation pulses comprises the informed stimulation pulse, and wherein the processing circuitry is configured to control the stimulation generation circuitry to interleave the plurality of control stimulation pulses with at least some of the plurality of informed stimulation pulses.

Example 52: the system of any combination of examples 44-51, wherein the processing circuitry is configured to control the stimulation generation circuitry to interleave the plurality of control stimulation pulses within at least some of the plurality of informed stimulation pulses by: controlling the stimulation generation circuitry to deliver at least two control stimulation pulses of the plurality of control stimulation pulses between consecutive informed stimulation pulses; and control sensing circuitry to sense, between the consecutive informed stimulation pulses, at least two ECAP signals elicited by respective control stimulation pulses of the at least two control stimulation pulses.

Example 53: the system of any combination of examples 44-52, wherein a pulse width of the informed stimulation pulse is greater than approximately 300 microseconds and less than approximately 1000 microseconds.

Example 54: the system of any combination of examples 44-53, wherein a pulse width of the control stimulation pulse is less than approximately 300 microseconds.

Example 55: the system of any combination of examples 44-54, wherein the informed stimulation pulse is a monophasic pulse followed by a passive recharge phase, and wherein the control stimulation pulse is a bi-phasic pulse comprising a positive phase and a negative phase.

Example 56: the system of any combination of examples 44-55, wherein the informed stimulation pulse is a first bi-phasic pulse comprising a first positive phase and a first negative phase, and wherein the control stimulation pulse is a second bi-phasic pulse comprising a second positive phase and a second negative phase.

Example 57: the system of any combination of examples 44-56, wherein the plurality of control pulses comprise a plurality of non-therapeutic pulses, and wherein the plurality of informed pulses comprise a plurality of therapy pulses.

Example 58: a computer-readable storage medium comprising instructions that, when executed, causes one or more processors to: control delivery of a control stimulation pulse to a patient, the control stimulation pulse having a first pulse width; sense an evoked compound action potential (ECAP) signal elicited by the control stimulation pulse; identify a characteristic of the ECAP signal; determine, based on the characteristic of the ECAP signal and a gain value, a therapy parameter value that at least partially defines a informed stimulation pulse from a plurality of informed pulses, wherein the plurality of informed pulses have a second pulse width longer than the first pulse width; and control delivery of the informed stimulation pulse according to the determined therapy parameter value.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A system comprising:
   stimulation generation circuitry configured to:
      deliver a first control stimulation pulse of a plurality of control stimulation pulses to a patient, the plurality of control stimulation pulses comprising a first frequency; and
      deliver a first informed stimulation pulse of a plurality of informed stimulation pulses to the patient, the plurality of informed stimulation pulses comprising a second frequency different than the first frequency; and
   processing circuitry configured to:
      receive a sensed evoked compound action potential (ECAP) signal elicited by the first control stimulation pulse;
      identify a characteristic of the ECAP signal;
      determine, based on the characteristic of the ECAP signal and a gain value, a second amplitude value that at least partially defines a second informed stimulation pulse of the plurality of informed stimulation pulses;
      determine a second amplitude value that at least partially defines a second control stimulation pulse of the plurality of control stimulation pulses to maintain a first ratio of a first amplitude value of the first control stimulation pulse to a first amplitude value of the first informed stimulation pulse being equal to a second ratio of the second amplitude value of the second control stimulation pulses to the second amplitude value of the second informed stimulation pulses; and
      control the stimulation generation circuitry to deliver the second control stimulation pulse according to the second amplitude value that at least partially defines the second control stimulation pulse and the second informed stimulation pulse of the plurality of informed stimulation pulses according to the second amplitude value that at least partially defines the second informed pulse.

2. The system of claim 1, wherein the stimulation generation circuitry is configured to deliver the plurality of control stimulation pulses at the first frequency over a period of time, and wherein the first frequency is within a range from 50 Hz to 400 Hz.

3. The system of claim 2, wherein the first frequency is within a range from 50 Hz to 60 Hz.

4. The system of claim 2, wherein the stimulation generation circuitry is configured to deliver the plurality of informed stimulation pulses at the second frequency over the period of time, and wherein the second frequency is greater than 400 Hz.

5. The system of claim 4, wherein the second frequency is within a range from 900 Hz to 1200 Hz.

6. The system of claim 1, wherein a second pulse width of the plurality of informed stimulation pulses is less than a first pulse width of the plurality of control stimulation pulses.

7. The system of claim 1, wherein the gain value represents a slope of a growth curve of values of the characteristic of ECAP signals elicited from respective calibration stimulation pulses delivered to the patient and at least partially defined by different values of a stimulation parameter.

8. The system of claim 1, wherein the characteristic of the ECAP signal is a measured amplitude of a portion of the ECAP signal, wherein to determine the second amplitude value of the second informed stimulation pulse, the processing circuitry is configured to:
- subtract the measured amplitude from a target ECAP amplitude value for the patient to generate a differential amplitude;
- multiply the differential amplitude by the gain value to generate a preliminary differential value;
- multiply the preliminary differential value by a scaling factor to generate a scaled differential value, wherein the scaling factor represents the first ratio; and
- add the scaled differential value to the first amplitude value of the first informed stimulation pulse to generate the second amplitude value of the second informed stimulation pulse.

9. The system of claim 8, wherein the measured amplitude of the portion of the ECAP signal comprises a voltage amplitude between an N1 peak and a P2 peak of the ECAP signal.

10. The system of claim 1, wherein to determine, based on the characteristic of the ECAP signal and the gain value, the second amplitude value that at least partially defines the second informed stimulation pulse, the processing circuitry is configured to:
- determine, based on an average value of a characteristic of a plurality of consecutively sensed ECAP signals and the gain value, the second amplitude value that at least partially defines the second informed stimulation pulse, the plurality of consecutively sensed ECAP signals comprising the ECAP signal.

11. The system of claim 1, wherein the processing circuitry is configured to interleave the plurality of control stimulation pulses with at least some of the plurality of informed stimulation pulses.

12. The system of claim 11, wherein to interleave the plurality of control stimulation pulses within at least some of the plurality of informed stimulation pulses, the processing circuitry is configured to:
- deliver at least two informed stimulation pulses of the plurality of informed stimulation pulses between consecutive control stimulation pulses; and
- sense, between the consecutive informed stimulation pulses, the ECAP signal elicited by the control stimulation pulse delivered between the consecutive informed stimulation pulses.

13. A method comprising:
- delivering a first control stimulation pulse of a plurality of control stimulation pulses to a patient, the plurality of control stimulation pulses comprising a first frequency;
- delivering a first informed stimulation pulse of a plurality of informed stimulation pulses to the patient, the plurality of informed stimulation pulses comprising a second frequency different than the first frequency;
- sensing an evoked compound action potential (ECAP) signal elicited by the first control stimulation pulse;
- identifying a characteristic of the ECAP signal;
- determining, based on the characteristic of the ECAP signal and a gain value, a second amplitude value that at least partially defines a second informed stimulation pulse of the plurality of informed stimulation pulses;
- determining a second amplitude value that at least partially defines a second control stimulation pulse of the plurality of control pulses to maintain a first ratio of a first amplitude value of the first control stimulation pulse to a first amplitude value of the first informed stimulation pulse being equal to a second ratio of the second amplitude value of the second control stimulation pulses to the second amplitude value of the second informed stimulation pulses; and
- delivering the second control stimulation pulse according to the second amplitude value that at least partially defines the second control stimulation pulse and the second informed stimulation pulse of the plurality of informed stimulation pulses according to the second amplitude value that at least partially defines the second informed pulse.

14. The method of claim 13, further comprising delivering the plurality of control stimulation pulses at the first frequency over a period of time, wherein the first frequency is within a range from 50 Hz to 400 Hz.

15. The method of claim 14, wherein the first frequency is within a range from 50 Hz to 60 Hz.

16. The method of claim 14, further comprising delivering the plurality of informed stimulation pulses at the second frequency over the period of time, wherein the second frequency is greater than 400 Hertz (Hz).

17. The method of claim 16, wherein the second frequency is within a range from 900 Hz to 1200 Hz.

18. The method of claim 13, wherein a second pulse width of the plurality of informed stimulation pulses is less than a first pulse width of the plurality of control stimulation pulses.

19. A non-transitory computer-readable storage medium comprising instructions that, when executed, causes one or more processors to:
- control delivery of a first control stimulation pulse of a plurality of control stimulation pulses to a patient, the plurality of control stimulation pulses comprising a first frequency;
- control delivery of a first informed stimulation pulse of a plurality of informed stimulation pulses to the patient, the plurality of informed stimulation pulses comprising a second frequency different than the first frequency;
- sense an evoked compound action potential (ECAP) signal elicited by the first control stimulation pulse;
- identify a characteristic of the ECAP signal;
- determine, based on the characteristic of the ECAP signal and a gain value, a second amplitude value that at least partially defines a second informed stimulation pulse of the plurality of informed stimulation pulses;
- determine a second amplitude value that at least partially defines a second control stimulation pulse of the plurality of control stimulation pulses to maintain a first ratio of a first amplitude value of the first control stimulation pulse to a first amplitude value of the first informed stimulation pulse being equal to a second ratio of the second amplitude value of the second control stimulation pulses to the second amplitude value of the second informed stimulation pulses; and
- control delivery of the second control stimulation pulse according to the second amplitude value that at least partially defines the second control stimulation pulse and the second informed stimulation pulse of the plurality of informed stimulation pulses according to the second amplitude value that at least partially defines the second informed pulse.

* * * * *